United States Patent
Tekumalla et al.

(10) Patent No.: US 10,448,898 B2
(45) Date of Patent: Oct. 22, 2019

(54) METHODS AND SYSTEMS FOR PREDICTING A HEALTH CONDITION OF A HUMAN SUBJECT

(71) Applicant: Conduent Business Services, LLC, Dallas, TX (US)

(72) Inventors: Lavanya Sita Tekumalla, Bangalore (IN); Vaibhav Rajan, Bangalore (IN)

(73) Assignee: CONDUENT BUSINESS SERVICES, LLC, Florham Park, NJ (US)

( * ) Notice: Subject to any disclaimer, the term of this patent is extended or adjusted under 35 U.S.C. 154(b) by 939 days.

(21) Appl. No.: 14/798,504

(22) Filed: Jul. 14, 2015

(65) Prior Publication Data
US 2017/0017769 A1 Jan. 19, 2017

(51) Int. Cl.
*A61B 5/00* (2006.01)
*G16H 50/30* (2018.01)
*G06F 19/00* (2018.01)

(52) U.S. Cl.
CPC ........... *A61B 5/7267* (2013.01); *G06F 19/00* (2013.01); *G16H 50/30* (2018.01)

(58) Field of Classification Search
CPC .... G06F 19/3431; G06F 19/00; G06F 16/285; G16H 50/70; G16H 50/30; G16H 10/60; G16H 50/20; A61B 5/7267
See application file for complete search history.

(56) References Cited

U.S. PATENT DOCUMENTS

| | | | | | |
|---|---|---|---|---|---|
| 4,783,803 | A | * | 11/1988 | Baker | ..................... G10L 15/00 704/252 |
| 2001/0051765 | A1 | * | 12/2001 | Walker | .................. A61B 5/1112 600/300 |
| 2005/0059017 | A1 | * | 3/2005 | Oldham | ..................... G01J 1/42 435/6.13 |
| 2005/0278140 | A1 | * | 12/2005 | Wang | ................. G01R 31/2894 702/179 |

(Continued)

OTHER PUBLICATIONS

Claudia Czado Aleksey Min. Bayesian inference for multivariate copulas using pair-copula constructions. Journal of Financial Econo-Metrics, pp. 511{546, 2010.

(Continued)

*Primary Examiner* — Neal Sereboff
(74) *Attorney, Agent, or Firm* — Jones Robb, PLLC

(57) ABSTRACT

Disclosed are embodiments of methods and systems for predicting a health condition of a first human subject. The method comprises extracting a historical data including physiological parameters of second human subjects. Thereafter, a first distribution of a first physiological parameter is determined based on a marginal cumulative distribution of a rank transformed historical data. Further, a second distribution of a second physiological parameter is determined based on the first distribution and a first conditional cumulative distribution of the rank transformed historical data. Further, a latent variable is determined based on the first and the second distributions. Thereafter, one or more parameters of at least one bivariate distribution, corresponding to a (Continued)

D-vine copula, are estimated based on the latent variable. Further, a classifier is trained based on the D-vine copula. The classifier is utilizable to predict the health condition of the first human subject based on his/her physiological parameters.

18 Claims, 7 Drawing Sheets

(56) References Cited

U.S. PATENT DOCUMENTS

| | | | | |
|---|---|---|---|---|
| 2011/0119212 | A1* | 5/2011 | De Bruin | A61B 5/00 706/12 |
| 2012/0095300 | A1* | 4/2012 | McNair | A61B 5/021 600/300 |
| 2012/0143017 | A1* | 6/2012 | Snyder | G06N 20/00 600/300 |
| 2012/0203166 | A1* | 8/2012 | Riback | A61B 5/14532 604/66 |
| 2012/0223889 | A1* | 9/2012 | Medlock | G06F 3/04883 345/168 |
| 2012/0288881 | A1* | 11/2012 | Liu | G01N 33/6893 435/7.92 |
| 2012/0290599 | A1* | 11/2012 | Tian | G06F 16/313 707/758 |

OTHER PUBLICATIONS

Paul Embrechts, Alexander McNeil, and Daniel Straumann. Correlation and dependence in risk management: properties and pitfalls. Risk management: value at risk and beyond, pp. 176{223, 2002.

Peter Hoff. Extending the rank likelihood for semiparametric copula estimation. The Annals of Applied Statistics, 1(1):265{283, 2007.

Harry Joe. Families of m-variate distributions with given margins and m(m-1)/2 bivariate dependence parameters. Lecture Notes—Monograph Series, pp. 120{141, 1996.

Ingmar Nolte. Modeling a multivariate transaction process. Journal of Financial Econometrics, 6(1):143{170, 2008.

Paul Embrechts, Filip Lindskog, and Alexander McNeil. Modelling dependence with copulas and applications to risk management. Handbook of heavy tailed distributions in _nance, 8(1):329{384, 2003.

Andrew J Patton. On the out-of-sample importance of skewness and asymmetric dependence for asset allocation. Journal of Financial Econometrics, 2(1):130{168, 2004.

C. Genest, K. Ghoudi, and L.-P. Rivest. A semiparametric estimation procedure of dependence parameters in multivariate families of distributions. Biometrika, 82(3):543{552, 1995.

* cited by examiner

METHODS AND SYSTEMS FOR PREDICTING A HEALTH CONDITION OF A HUMAN SUBJECT

TECHNICAL FIELD

The presently disclosed embodiments are related, in general, to healthcare. More particularly, the presently disclosed embodiments are related to methods and systems for predicting a health condition of a human subject.

BACKGROUND

Various industries, such as the healthcare industry, may churn out an enormous amount of data related to the various stakeholders of the industry. Analysing such enormous data to draw meaningful trends and insights therefrom may be an important task for various players of the industry for deriving competitive advantage. Various mathematical models may be used to identify trends and categorize the data into well-defined categories. For instance, the healthcare industry may maintain various records of human subjects/patients such as, but not limited to, medical diagnosis records, medical insurance records, hospital data, etc. Based on one or more mathematical models, the records of the human subjects/patients may be classified into various categories such as health conditions of human subjects/patients, health insurance fraud risks, and so on.

Typically, the data, which is to be analysed, may include fields of various types. For example, the medical records may include various fields of numerical data type, for instance, BP measure, heart rate, and blood sugar measure. Further, the medical records may also include various fields of categorical data type, for example, gender. The mathematical models used to analyse such records may only consider the data of numerical data type to identify the trends and categorize them. Further, analysis of records having a large number of fields may as such be a cumbersome task.

SUMMARY

According to embodiments illustrated herein there is provided a method for predicting a health condition of a first human subject. The method comprises receiving, by one or more processors, a measure of one or more physiological parameters associated with the first human subject. The one or more physiological parameters include at least one of an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood haemoglobin level, and a blood platelet count. The method further comprises extracting, by the one or more processors, a historical data comprising a measure of the one or more physiological parameters associated with each of one or more second human subjects. Thereafter, a first distribution associated with a first physiological parameter, from the one or more physiological parameters, is determined based on a marginal cumulative distribution of a transformed historical data. The transformed historical data is determined by ranking of the historical data. Further, a second distribution associated with a second physiological parameter, from the one or more physiological parameters, is determined based on the first distribution and a first conditional cumulative distribution of the transformed historical data. The first conditional cumulative distribution is deterministic of at least an association between the first physiological parameter and the second physiological parameter. Further, a latent variable is determined based at least on the first distribution and the second distribution. Thereafter, one or more parameters of at least one bivariate distribution are estimated based at least on the latent variable, wherein the at least one bivariate distribution corresponds to a D-vine copula. The D-vine copula is deterministic of one or more health conditions associated with each of the one or more second human subjects in the historical data. Further, a classifier is trained based on the D-vine copula. Thereafter, the health condition of the first human subject is predicted by utilizing the classifier based on the received measure of the one or more physiological parameters associated with the first human subject.

According to embodiment illustrated herein there is provided a system for predicting a health condition of a first human subject. The system comprising one or more processors configured to receive a measure of one or more physiological parameters associated with the first human subject. The one or more physiological parameters include at least one of an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood hemoglobin level, and a blood platelet count. The one or more processors are further configured to extract a historical data comprising a measure of the one or more physiological parameters associated with each of one or more second human subjects. Thereafter, a first distribution associated with a first physiological parameter, from the one or more physiological parameters, is determined based on a marginal cumulative distribution of a transformed historical data. The transformed historical data is determined by ranking of the historical data. Further, a second distribution associated with a second physiological parameter, from the one or more physiological parameters, is determined based on the first distribution and a first conditional cumulative distribution of the transformed historical data. The first conditional cumulative distribution is deterministic of at least an association between the first physiological parameter and the second physiological parameter. Further, a latent variable is determined based at least on the first distribution and the second distribution. Thereafter, one or more parameters of at least one bivariate distribution are estimated based at least on the latent variable, wherein the at least one bivariate distribution corresponds to a D-vine copula. The D-vine copula is deterministic of one or more health conditions associated with each of the one or more second human subjects in the historical data. Further, a classifier is trained based on the D-vine copula. A measure of the one or more physiological parameters associated with the first human subject are received. Thereafter, the health condition of the first human subject is predicted by utilizing the classifier based on the received measure of the one or more physiological parameters associated with the first human subject.

According to embodiment illustrated herein there is provided a computer program product for use with a computing device. The computer program product comprising a non-transitory computer readable medium. The non-transitory computer readable medium stores a computer program code for predicting a health condition of a first human subject. The computer program code is executable by one or more processors in the computing device to receive a measure of one or more physiological parameters associated with the first human subject. The one or more physiological parameters include at least one of an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood hemoglobin level, and a blood platelet count. The computer program code is further executable by the one or more processors to extract a historical data comprising a measure of one or more physiological parameters associated with each of one or more second human subjects. Thereafter, a first distribution associated with a first physiological parameter, from the one or more physiological parameters, is determined based on a marginal cumulative distribution of a transformed historical data. The transformed historical data is determined by ranking of the historical data. Further, a second distribution associated with a second physiological parameter, from the one or more physiological parameters, is determined based on the first distribution and a first conditional cumulative distribution of the transformed historical data. The first conditional cumulative distribution is deterministic of at least an association between the first physiological parameter and the second physiological parameter. Further, a latent variable is determined based at least on the first distribution and the second distribution. Thereafter, one or more parameters of at least one bivariate distribution are estimated based at least on the latent variable, wherein the at least one bivariate distribution corresponds to a D-vine copula. The D-vine copula is deterministic of one or more health conditions associated with each of the one or more second human subjects in the historical data. Further, a classifier is trained based on the D-vine copula. A measure of the one or more physiological parameters associated with the first human subject are received. Thereafter, the health condition of the first human subject is predicted by utilizing the classifier based on the received measure of the one or more physiological parameters associated with the first human subject.

BRIEF DESCRIPTION OF DRAWINGS

The accompanying drawings illustrate various embodiments of systems, methods, and other aspects of the disclosure. Any person having ordinary skill in the art will appreciate that the illustrated element boundaries (e.g., boxes, groups of boxes, or other shapes) in the figures represent one example of the boundaries. It may be that in some examples, one element may be designed as multiple elements or that multiple elements may be designed as one element. In some examples, an element shown as an internal component of one element may be implemented as an external component in another, and vice versa. Furthermore, elements may not be drawn to scale.

Various embodiments will hereinafter be described in accordance with the appended drawings, which are provided to illustrate, and not limit, the scope in any manner, wherein similar designations denote similar elements, and in which.

DETAILED DESCRIPTION

Figure 1:
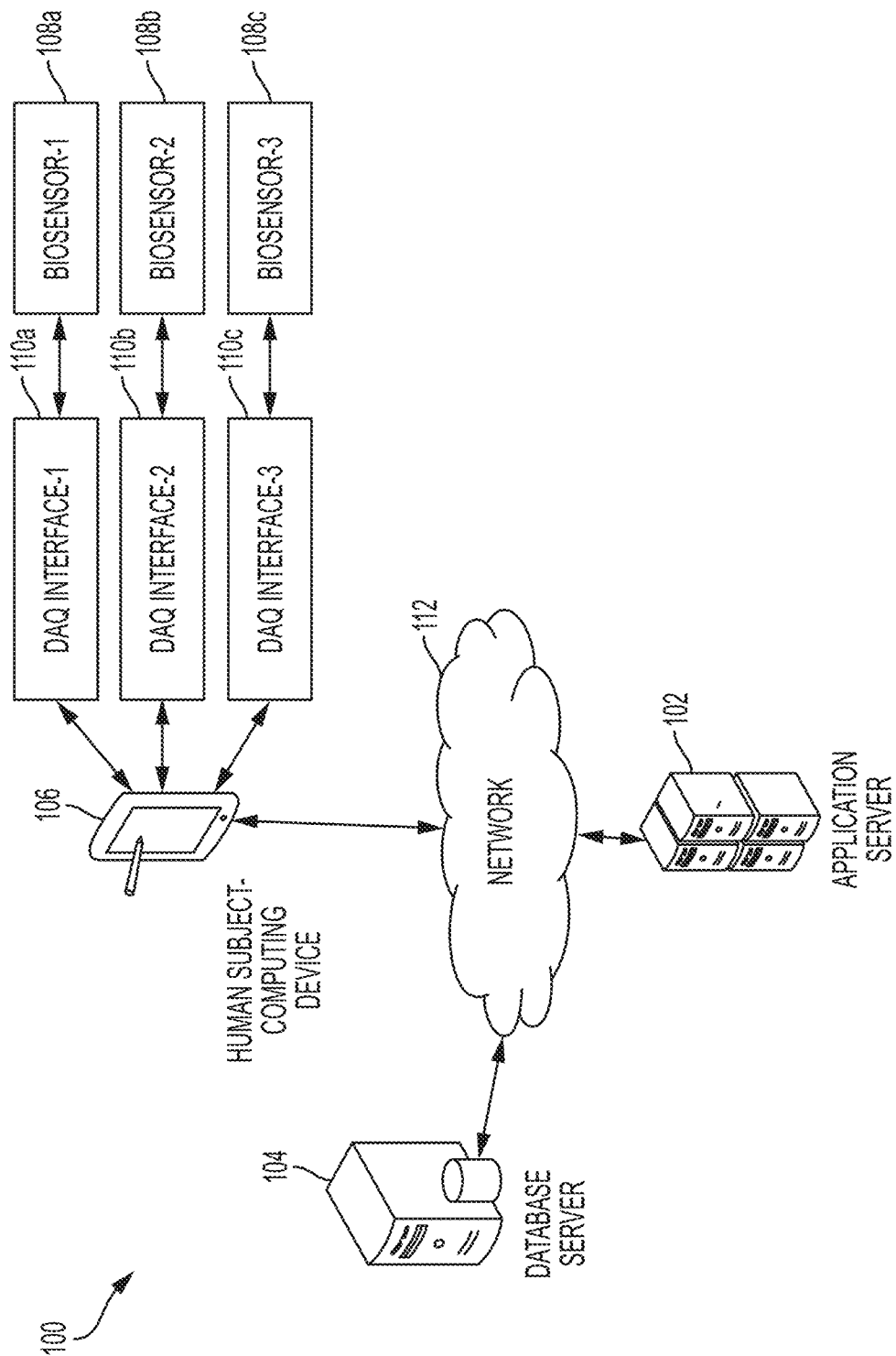
FIG. 1 is a block diagram of a system environment, in which various embodiments can be implemented.

The present disclosure is best understood with reference to the detailed figures and descriptions set forth herein. Various embodiments are discussed below with reference to the figures. However, those skilled in the art will readily appreciate that the detailed descriptions given herein with respect to the figures are simply for explanatory purposes, as the methods and systems may extend beyond the described embodiments. For example, the teachings presented and the needs of a particular application may yield multiple alternate and suitable approaches to implement the functionality of any detail described herein. Therefore, any approach may extend beyond the particular implementation choices in the following embodiments described and shown.

References to "one embodiment," "at least one embodiment," "an embodiment," "one example", "an example", "for example" and so on, indicate that the embodiment(s) or example(s) so described may include a particular feature, structure, characteristic, property, element, or limitation, but that not every embodiment or example necessarily includes that particular feature, structure, characteristic, property, element, or limitation. Furthermore, repeated use of the phrase "in an embodiment" does not necessarily refer to the same embodiment.

Definitions: The following terms shall have, for the purposes of this application, the respective meanings set forth below.

A "multivariate dataset" refers to a dataset that includes observations of an m-dimensional variable. For example, "n" observations of m-dimensional variable may constitute a multivariate dataset. For example, a medical record data may include a measure of one or more physiological parameters of one or more patients, where the one or more physiological parameters correspond to the m-dimensions and the one or more patients correspond to n observations. Such medical record data is an example of the multivariate dataset.

A "healthcare dataset" refers to a multivariate dataset that includes data obtained from the healthcare industry. In an embodiment, the healthcare dataset may correspond to a patient record data, hospital data, medical insurance data, diagnostics data, etc. In a scenario, where the healthcare data corresponds to the patient record data, the one or more physiological parameters correspond to the m-dimensional variable, and the number of records in the healthcare data corresponds to the observations.

A "human subject" corresponds to a human being, who may have a health condition or a disease. In an embodiment, the human subject may correspond to a person who seeks a medical opinion on his/her health condition.

A "Data-Acquisition (DAQ) device" refers to a device, which may gather signals from an external stimulus and generate output usable by a computing device for further processing. For example, a DAQ device may correspond to a temperature sensor that measures a surface temperature of a substrate and generates a corresponding temperature reading for further processing by a computing device.

A "DAQ interface" refers to an interface that facilitates communication between a DAQ device and a computing device. In an embodiment, to facilitate communication between a DAQ device and a computing device connected through the DAQ interface, the DAQ interface may convert a signal of a first format, generated by the DAQ device, to a signal of a second format, acceptable by the computing device, and vice versa. For instance, the DAQ interface may convert analogue signals generated by a DAQ device to corresponding digital signals, acceptable by a computing device. Further, the DAQ interface may serialize or parallelize the digital signals in accordance with data-input requirements of the computing device. Examples of the DAQ interface include, but are not limited to, a Universal Serial Bus (USB) Port, a FireWire Port, an IEEE 1394 standard based connector, or any other serial/parallel data interfacing connector known in the art.

"Biosensor" refers to a DAQ device usable to measure one or more physiological parameters of a human subject. Examples of a biosensor include, but are not limited to, a pressure/pulse sensor (to measure a blood pressure and heart rate), a temperature sensor (to measure a body temperature), a blood sample analyzer (to measure readings of various blood-tests such as a blood creatinine level, a blood albumin level, a blood sodium level, a total blood count, a blood glucose/sugar level, a blood hemoglobin level, and a blood platelet count, a cholesterol level), a breath analyzer (to measure a breath carbon-dioxide/oxygen concentration), and so on.

A "copula" refers to a multivariate probability distribution of a multivariate dataset, which may be used to decouple dependencies among the various dimensions of the multivariate dataset. In an embodiment, the copula may be represented as a function of constituent univariate marginal distributions of the various dimensions in the multivariate dataset. In an embodiment, the univariate marginal distributions may be uniformly distributed. In an embodiment, an m-dimensional copula may be represented as a multivariate distribution function $C: [0,1]^m \rightarrow [0,1]$. The following equation represents a relationship between a joint distribution function F and univariate marginal distributions $F_1(X_1)$, $F_2(X_2), \ldots F_m(X_m)$ of an m-dimensional multivariate dataset using an m-dimensional Copula function C:

$$F(X_1, X_2, \ldots X_m) = C(F_1(X_1), F_2(X_2), \ldots F_m(X_m)) \quad (1)$$

where, $X_i$: a random variable for the $i^{th}$ dimension of the m-dimensional multivariate dataset (e.g., a measure of a physiological parameter in a multivariate healthcare dataset);

$F_i(X_i)$: a univariate marginal distribution for the dimension of the m-dimensional multivariate dataset, where $U_i \leq F_i(X_i)$, $U_i$: a cumulative distribution of $X_i$;

F( ): a joint distribution function of the m-dimensional multivariate dataset; and C( ): an m-dimensional copula function.

A "joint density function" refers to a joint probability distribution of a multivariate dataset. In an embodiment, the joint density function may represent a probability of assigning values to the various dimensions of the multivariate dataset within a respective range associated with each dimension. In an embodiment, a joint density function f of a m-dimensional multivariate dataset may be expressed in terms of an m-dimensional copula density function $c_{1 \ldots m}$ and univariate marginal density functions $f_1, f_2, \ldots f_m$ as follows:

$$f(X_1, X_2, \ldots X_m) = c_{1 \ldots m}(F_1(X_1), F_2(X_2), \ldots F_m(X_m)) \cdot f_1(X_1) \cdot f_2(X_2) \ldots f_m(X_m) \quad (2)$$

where, f( ): a joint density function of the m-dimensional multivariate dataset;

$f_i(X_i)$: a marginal density function of $X_i$; and $c_{1 \ldots m}$: an m-dimensional copula density function, where $$c_{1 \ldots m}(F_1(X_1), F_2(X_2), \ldots F_m(X_m)) = \frac{\delta C}{\delta F_1 \delta F_2 \ldots \delta F_m} C(F_1(X_1), F_2(X_2), \ldots F_m(X_m)) \quad (3)$$

In an embodiment, the joint density function f of the m-dimensional multivariate dataset may also be expressed in terms of conditional densities of the random variables as follows:

$$f(X_1, X_2, \ldots X_m) = f_m(X_m) \cdot f(X_{m-1}|X_m) \ldots f(X_1|X_2, \ldots X_m) \quad (4)$$

where, $f(X_l|X_{l+1}, \ldots X_{l+j-1})$: a conditional density of the random variable $X_l$ (for the $l^{th}$ dimension), where $1 \leq l \leq m-1$ and $j = m-1$.

By simplifying the equations 2, 3, and 4, the joint density function f may be expressed in terms of univariate marginal density functions $f_1, f_2, \ldots f_m$ and bivariate copula densities as follows:

$$f(X_1, X_2, \ldots X_m) = \Pi_{k=1}^m f_k(X_k) \Pi_{j=1}^{m-1} \Pi_{l=1}^{m-j} c_{l,l+j|l+1, \ldots l+j-1}(F(X_l|X_{l+1}, \ldots X_{l+j-1}), F(X_{l+j}|X_{l+1}, \ldots X_{l+j-1})) \quad (5)$$

where, $c_{l,l+j|l+1, \ldots l+j-1}$: a density of a bivariate copula distribution $c_{l,l+j|l+1, \ldots l+j-1}$; and $F(X_l|X_{l+1}, \ldots X_{l+j-1})$: a conditional cumulative distribution of the random variable $X_l$.

A "bivariate copula distribution" refers to a copula distribution that may model a dependency between a pair of dimensions of a multivariate dataset. Examples of the bivariate copula distribution may include, but are not limited to, a T-student copula distribution, a Clayton copula distribution, a Gumbel copula distribution, or a Gaussian copula distribution. In an embodiment, the bivariate copula distribution may be a part of a D-vine copula distribution.

A "D-vine copula" refers to a hierarchal collection of bivariate copula distributions. In an embodiment, the D-vine copula may be represented graphically by a set of hierarchal trees, each of which may include a set of nodes arranged sequentially and connected by a set of edges. Further, each edge, connecting a pair of nodes in a hierarchal tree, may represent a bivariate copula distribution. In an embodiment, for "m" random variables, the D-vine copula may correspond to a hierarchal structure including m−1 hierarchal trees representing a total of $$\frac{m(m-1)}{2}$$

bivariate copula distributions. For example, a D-vine copula may be used to represent the bivariate copula distributions of the equation 5. In such a scenario, the variable j in the equation 5 may identify a hierarchal tree of the D-vine copula and the variable l in the equation 5 may identify an edge within that hierarchal tree, for representing each bivariate copula distribution of the equation 5 through the D-vine copula. In an embodiment, the D-vine copula may model a dependency between each pair of dimensions in a multivariate dataset. In an embodiment, the constituent bivariate copula distributions within the D-vine copula model may belong to different families of copula functions. Examples of the various families of copula functions include, but are not limited to, a T-student copula distribution, a Clayton copula distribution, a Gumbel copula distribution, or a Gaussian copula distribution.

An "h-function" refers to a conditional distribution of a random variable in terms of a bivariate copula distribution with known parameters. In an embodiment, the h-function may be used to represent an m-dimensional conditional distribution in terms of a pair of (m−1)-dimensional conditional distributions. Thus, the h-function may be used to recursively evaluate a conditional distribution in terms of individual random variables representing the various dimensions of the original conditional distribution. The following equation is an example of a conditional cumulative distribution function represented in terms of an h-function:

$$F(X_j|X_1, \ldots X_{j-1}) = \qquad (6)$$

$$\frac{\delta C_{j,1|2,\ldots,j-1}(F(X_j|X_2, \ldots X_{j-1}), F(X_1|X_2, \ldots X_{j-1}))}{\delta F(X_1|X_2, \ldots X_{j-1})} =$$

$$h(F(X_j|X_2, \ldots X_{j-1}), F(X_1|X_2, \ldots X_{j-1})); \Sigma_{j,1|2\ldots j-1}$$

where, $F(X_j|X_1, \ldots X_{j-1})$: a conditional cumulative distribution of $X_j$;

$C_{j,1|2, \ldots, j-1}$: a bivariate copula distribution between $j^{th}$ and $1^{st}$ dimensions, conditioned on $2^{nd}$, $3^{rd}$, ... $(j-1)^{th}$ parameters;

$\Sigma_{j,1|2 \ldots j-1}$: parameters of the bivariate copula distribution $C_{j,1|2, \ldots, j-1}$, which may be pre-estimated; and h( ): h function.

A person skilled in the art will understand that a conditional cumulative distribution of random variable may be equivalent to a conditional cumulative distribution of the corresponding marginal distribution of the random variable. Hence, an h-function in terms of the random variable may be equivalent to an h-function in terms of the corresponding marginal distribution of the random variable. For instance, $X_1$ and $X_2$ are random variables with corresponding marginal distributions $U_1=F_1(X_1)$ and $U_2=F_2(X_2)$. Then, $F(U_1|U_2)=F(X_1|X_2)=h(X_1,X_2)=h(U_1,U_2)$.

A "cumulative distribution" refers to a distribution function, that describes the probability that a real-valued random variable X with a given probability distribution will be found at a value less than or equal to x.

A "marginal cumulative distribution" refers to a cumulative distribution of a random variable representing a single dimension of a multivariate dataset. For example, $X_i$ is a random variable representing an $i^{th}$ dimension of the multivariate dataset. The marginal cumulative distribution of $X_i$ may be represented as $F_i(X_i)$ or $U_i$.

A "conditional cumulative distribution" refers to a multivariate cumulative distribution of multiple random variables, which is conditioned on at least one of the random variable. For example, $F(X_3|X_2, X_1)$ is a three dimensional conditional cumulative distribution of random variables $X_1$, $X_2$, and $X_3$ such that the marginal cumulative distribution of the random variable $X_3$ may be conditioned on the marginal cumulative distributions of the random variables $X_1$ and $X_2$.

An "inverse cumulative distribution" refers to an inverse function of the cumulative distribution of the random variable X.

A "latent variable" refers to an intermediate variable that may not be directly obtainable from a multivariate dataset. In an embodiment, the latent variable may be determined based on one or more parameters of a distribution representing the multivariate dataset. For example, a latent variable (e.g., U) may be determined based on a marginal cumulative distribution (e.g., $F_i(X_i)$'s) of each dimension (e.g., $X_i$'s) in the multivariate dataset.

"Probability" shall be broadly construed, to include any calculation of probability; approximation of probability, using any type of input data, regardless of precision or lack of precision; any number, either calculated or predetermined, that simulates a probability; or any method step having an effect of using or finding some data having some relation to a probability.

A "random variable" refers to a variable that may be assigned a value probabilistically or stochastically.

A "classifier" refers to a mathematical model that may be configured to categorize data into one or more categories. In an embodiment, the classifier is trained based on historical data. Examples of the classifier may include, but are not limited to, a Support Vector Machine (SVM), a Logistic Regression, a Bayesian Classifier, a Decision Tree Classifier, a Copula-based Classifier, a K-Nearest Neighbors (KNN) Classifier, or a Random Forest (RF) Classifier.

"Training" refers to a process of updating/tuning a classifier using a historical data such that the classifier is able to predict the one or more categories in the historical data with a greater accuracy.

"Gibbs sampling" refers to a statistical technique that may be used to generate samples from a multivariate distribution. In an embodiment, Gibbs sampling corresponds to a Markov Chain Monte Carlo (MCMC) algorithm for obtaining a sequence of observations from a joint distribution of two or more univariate marginal distributions, when direct sampling from the multivariate distribution may be difficult.

"Expectation Maximization (EM) algorithm" refers to a statistical technique of determining a maximum likelihood estimate of one or more parameters of a distribution, where the distribution depends on unobserved latent variables.

FIG. 1 is a block diagram illustrating a system environment 100 in which various embodiments may be implemented. The system environment 100 includes an application server 102, a database server 104, a human subject-computing device 106, and a network 112.

The application server 102 refers to a computing device including one or more processors and one or more memories. The one or more memories may include computer readable code that is executable by the one or more processors to perform predetermined operation. In an embodiment, the predetermined operation may include predicting a health condition of a first human subject. In an embodiment, the application server 102 may extract a historical data comprising medical records of one or more second human subjects from the database server 104. In an embodiment, a medical record associated with a human subject may include a measure of one or more physiological parameters associated with the human subject.

In an embodiment, the application server 102 may apply a rank transformation on the historical data to determine a transformed historical data using an extended rank likelihood technique. The application server 102 may determine a first distribution of a first physiological parameter, from the one or more physiological parameters, based on a marginal cumulative distribution of the transformed historical data. Further, the application server 102 may determine a second distribution of a second physiological parameter, from the one or more physiological parameters, based on the first distribution and a first conditional cumulative distribution of the transformed historical data. In an embodiment, the first conditional cumulative distribution may be deterministic at least of a relation between the first physiological parameter and the second physiological parameter.

Thereafter, in an embodiment, the application server 102 may determine a latent variable based on at least the first distribution and the second distribution. Further, the application server 102 may estimate one or more parameters of a bivariate distribution of the first and the second physiological parameters based on the latent variable. In an embodiment, the bivariate distribution may be a bivariate copula distribution associated with a D-vine copula distribution model. In an embodiment, the D-vine copula may include a hierarchal collection of bivariate copula distributions, which may be used to model dependencies among each pair of physiological parameters in the historical data. In an embodiment, the application server 102 may determine the various bivariate copula distributions associated with the D-vine copula distribution. Thereafter, in an embodiment, the application server 102 may train a classifier based on the D-vine copula distribution. The D-vine copula distribution may be deterministic of the one or more health conditions of the one or more second human subjects in the historical data. The training of the classifier based on the D-vine copula distribution has been explained further in conjunction with FIG. 3A and FIG. 3B.

Thereafter, in an embodiment, the application server 102 may receive a measure of the one or more physiological parameters of the first human subject from the human subject-computing device 106 of the first human subject. Alternatively, in a scenario where the one or more physiological parameters of the first human subject are stored on the database server 104, the application server 102 may extract the one or more parameters of the first human subject from the database server 104. In another embodiment, the application server 102 may include one or more biosensors or may be communicatively coupled to the one or more biosensors. The one or more biosensors may determine the measure of the one or more physiological parameters of the first human subject.

Thereafter, based on the measure of the one or more physiological parameters of the first human subject, the application server 102 may predict the health condition of the first human subject using the classifier. The application server 102 may then display the predicted health condition of the first human subject through a user-interface on the human subject-computing device 106. The prediction of the health condition of the first human subject has been explained further in conjunction with FIG. 4.

The application server 102 may be realized through various types of application servers such as, but not limited to, Java application server, .NET framework application server, and Base4 application server.

The database server 104 may refer to a computing device, which stores at least the historical data including the medical records of the one or more second human subjects. In addition, in an embodiment, the database server 104 may also store the one or more physiological parameters of the first human subject, which may be received from the human-subject computing device 106 of the first human subject. In an embodiment, the database server 104 may receive a query from the application server 102 to extract the information stored on the database server 104. The database server 104 may be realized through various technologies such as, but not limited to, Oracle®, IBM DB2®, Microsoft SQL Server®, Microsoft Access®, PostgreSQL®, MySQL® and SQLite®, and the like. In an embodiment, the application server 102 may connect to the database server 104 using one or more protocols such as, but not limited to, Open Database Connectivity (ODBC) protocol and Java Database Connectivity (JDBC) protocol.

A person with ordinary skill in the art would understand that the scope of the disclosure is not limited to the database server 104 as a separate entity. In an embodiment, the functionalities of the database server 104 can be integrated into the application server 102.

The human subject-computing device 106 refers to a computing device used by a human subject (such as the first human subject and the one or more second human subjects). The human subject-computing device 106 may include one or more processors and one or more memories. The one or more memories may include computer readable code that is executable by the one or more processors to perform predetermined operation. In an embodiment, one or more biosensors (e.g., a biosensor-1 108a, a biosensor-2 108b, and a biosensor-3 108c) may be inbuilt within the human subject-computing device 106. Alternatively, the one or more biosensors (e.g., a biosensor-1 108a, a biosensor-2 108b, and a biosensor-3 108c) may be coupled to the human subject-computing device 106 through one or more data acquisition (DAQ) interfaces (e.g., a DAQ interface-1 110a, a DAQ interface-2 110b, and a DAQ interface-3 110c). For instance, as shown in FIG. 1, the DAQ interface-1 110a may connect the biosensor-1 108a with the human subject-computing device 106. Similarly, the DAQ interface-2 110b may connect the biosensor-2 108b with the human subject-computing device 106, and so on. In another embodiment, the one or more biosensors, for example, 108a, may be connected to the human subject-computing device 106 through a wireless connection such as, but not limited to, a Bluetooth based connection, a Near Field Communication (NFC) based connection, a Radio Frequency Identification (RFID) based connection, or any other wireless communication protocol.

In an embodiment, the one or more biosensors (e.g., 108a-108c) may refer to DAQ devices usable to gather various signals from a human subject and generate corresponding readings of the one or more physiological parameter of the human subject. Examples of the one or more physiological parameters include, but are not limited to, an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood hemoglobin level, and a blood platelet count. In an embodiment, the one or more biosensors (e.g., 108a-108c) may be attached to a body of the human subject to measure the one or more physiological parameters of the human subject. Examples of such biosensors include, but are not limited to, a blood pressure/pulse sensor, or a temperature sensor. Alternatively, the one or more biosensors (e.g., 108a-108c) may correspond to one or more blood sample analyzers for analyzing a blood sample taken from the human subject to determine readings of one or more blood tests. In another embodiment, the one or more biosensors (e.g., 108a-108c) may correspond to one or more breath analyzers for analyzing a breath sample of the human subject.

In an embodiment, the one or more DAQ interfaces (e.g., 110a-110c) may connect the one or more biosensors (e.g., 108a-108c) with the human-subject computing device 106. Further, the one or more DAQ interfaces (e.g., 110a-110c) may facilitate communication between each of the one or more biosensors (e.g., 108a-108c) and the human-subject computing device 106. In an embodiment, to facilitate communication between each biosensor (e.g., 108a) and the human-subject computing device 106 connected through a respective DAQ interface (e.g., 110a), the respective DAQ interface (e.g., 110a) may convert a signal of a first format, generated by the biosensor (e.g., 108a), to a signal of a second format, acceptable by the human-subject computing device 106, and vice versa. For instance, the DAQ interface (e.g., 110a) may convert analogue signals generated by the biosensor (e.g., 108a) to corresponding digital signals, acceptable by the human-subject computing device 106. Further, the DAQ interface (e.g., 110a) may serialize or parallelize the digital signals in accordance with data-input requirements of the human-subject computing device 106. For instance, the DAQ interface (e.g., 110a) may parallelize digital signals into 32-bit data words if the human-subject computing device 106 accepts digital data in a 32-bit format. Examples of the DAQ interface include, but are not limited to, a Universal Serial Bus (USB) Port, a FireWire Port, an IEEE 1394 standard based connector, or any other serial/parallel data interfacing connector known in the art.

In an embodiment, the human subject-computing device 106 may transmit the measure of the one or more physiological parameters of the human subject to at least one of the application server 102 or the database server 104. In an embodiment, the application server 102 may predict a health condition of the human subject, as described above. Thereafter, the human subject-computing device 106 may display the predicted health condition of the human subject through a user-interface on a display device of the human subject-computing device 106. Based on the predicted health condition of the human subject, the human subject may consult with a medical practitioner.

A person skilled in the art will understand that the scope of the disclosure is not limited to the human subject-computing device 106 being used by the human subject. In an embodiment, the human subject-computing device 106 may be used by a medical practitioner. In such a scenario, when a human subject visits the medical practitioner for a consultation, the medical practitioner may use the human subject-computing device 106 to measure the one or more physiological parameters of the human subject. Thereafter, the human subject-computing device 106 may transmit the one or more physiological parameters of the human subject to at least one of the application server 102 or the database server 104. The application server 102 may predict a health condition of the human subject, as described above. Thereafter, the human subject-computing device 106 may display the predicted health condition of the human subject through the user-interface on a display device of the human subject-computing device 106. Based on the predicted health condition of the human subject, the medical practitioner may recommend a treatment course including one or more medicines, one or more clinical/pathological tests, or one or more diet plans to the human subject.

The human subject-computing device 106 may include a variety of computing devices such as, but not limited to, a laptop, a personal digital assistant (PDA), a tablet computer, a smartphone, a phablet, and the like.

A person skilled in the art will understand that the scope of the disclosure is not limited to the human subject-computing device 106 and the application server 102 as separate entities. In an embodiment, the application server 102 may be realized as an application hosted on or running on the human subject-computing device 106 without departing from the spirit of the disclosure.

The network 112 corresponds to a medium through which content and messages flow between various devices of the system environment 100 (e.g., the application server 102, the database server 104, and the human subject-computing device 106). Examples of the network 112 may include, but are not limited to, a Wireless Fidelity (Wi-Fi) network, a Wireless Area Network (WAN), a Local Area Network (LAN), or a Metropolitan Area Network (MAN). Various devices in the system environment 100 can connect to the network 112 in accordance with various wired and wireless communication protocols such as Transmission Control Protocol and Internet Protocol (TCP/IP), User Datagram Protocol (UDP), and 2G, 3G, or 4G communication protocols.

Figure 2:
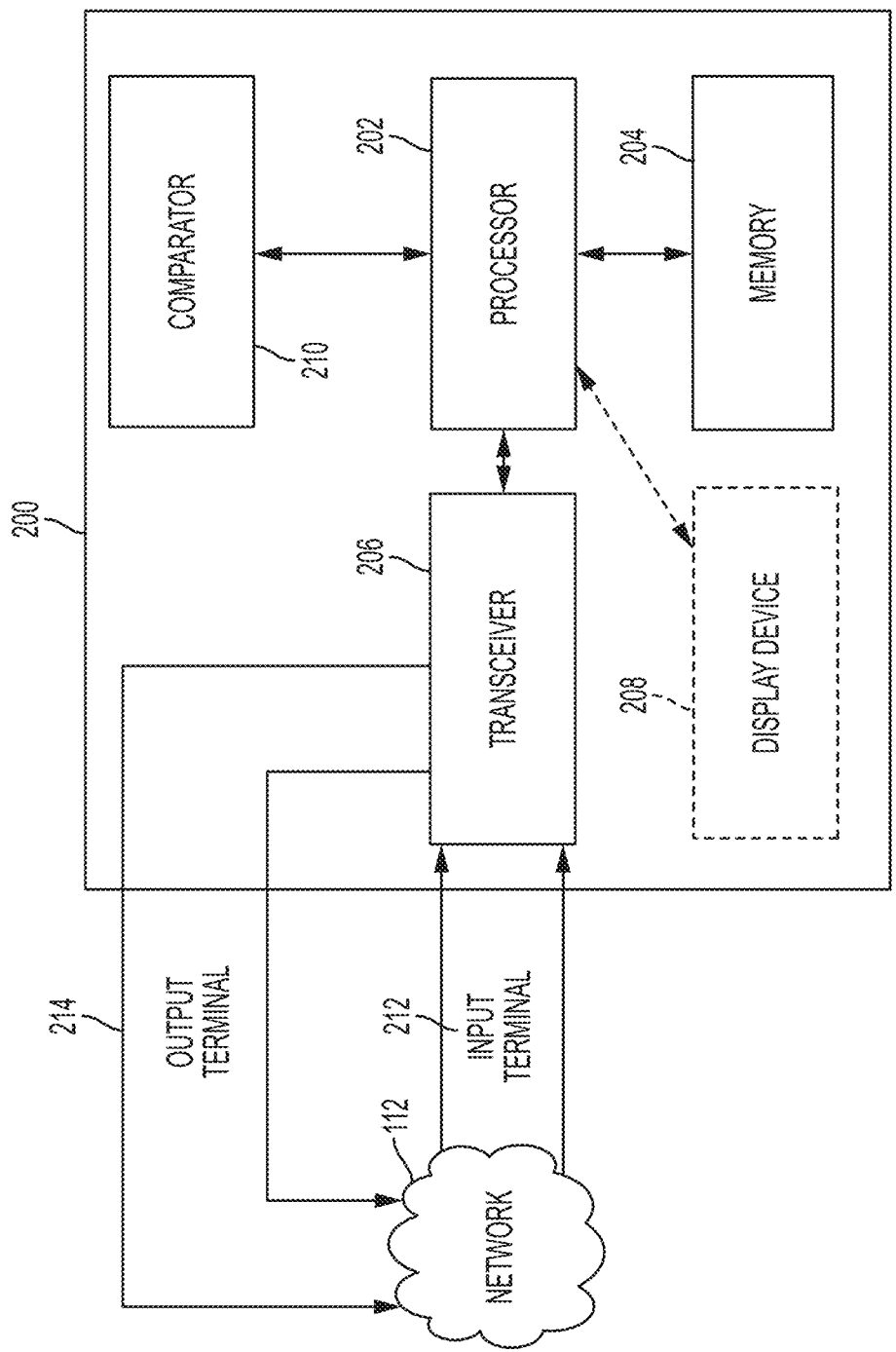
FIG. 2 is a block diagram of a system that is capable of identifying one or more clusters in a multivariate dataset, in accordance with at least one embodiment.

FIG. 2 is a block diagram of a system 200 that is capable of identifying one or more clusters in a multivariate dataset, in accordance with at least one embodiment. In an embodiment, the system 200 may correspond to the application server 102 or the human subject-computing device 106. For the purpose of ongoing description, the system 200 is considered the application server 102. However, the scope of the disclosure should not be limited to the system 200 as the application server 102. The system 200 may also be realized as the human subject-computing device 106, without departing from the spirit of the disclosure.

The system 200 includes a processor 202, a memory 204, a transceiver 206, a display 208, and a comparator 210. The processor 202 is coupled to the memory 204 and the transceiver 206. The transceiver 206 is coupled to a network 112 through an input terminal 212 and an output terminal 214.

The processor 202 includes suitable logic, circuitry, and interfaces and is configured to execute one or more instructions stored in the memory 204 to perform predetermined operations on the computing device 100. The memory 204 may be configured to store the one or more instructions. The processor 202 may be implemented using one or more processor technologies known in the art. Examples of the processor 202 include, but are not limited to, an X86 processor, a RISC processor, an ASIC processor, a CISC processor, or any other processor.

The memory 204 stores a set of instructions and data. Some of the commonly known memory implementations include, but are not limited to, a RAM, a read-only memory (ROM), a hard disk drive (HDD), and a secure digital (SD) card. Further, the memory 204 includes the one or more instructions that are executable by the processor 202 to perform specific operations. It is apparent to a person having ordinary skill in the art that the one or more instructions stored in the memory 204 enable the hardware of the computing device 100 to perform the predetermined operations.

The transceiver 206 transmits and receives messages and data to/from one or more computing devices connected to the computing device 100 over the network 112. Examples of the network 112 may include, but are not limited to, a Wireless Fidelity (Wi-Fi) network, a Wireless Area Network (WAN), a Local Area Network (LAN), or a Metropolitan Area Network (MAN). In an embodiment, the transceiver 206 is coupled to the network 112 through the input terminal 212 and the output terminal 214, through which the transceiver 206 may receive and transmit data/messages respectively. Examples of the transceiver 206 may include, but are not limited to, an antenna, an Ethernet port, a USB port, or any other port that can be configured to receive and transmit data. The transceiver 206 transmits and receives data/messages in accordance with the various communication protocols such as, TCP/IP, UDP, and 2G, 3G, or 4G communication protocols.

The display 208 facilitates a user of the computing device 100 to view information presented on the computing device 100. For example, the user may view a multivariate dataset and one or more clusters identified in the multivariate dataset on the display 208. The display 208 may be realized through several known technologies, such as Cathode Ray Tube (CRT) based display, Liquid Crystal Display (LCD), Light Emitting Diode (LED) based display, Organic LED based display, and Retina Display® technology. In an embodiment, the display 208 can be a touch screen that is operable to receive a user-input.

The comparator 210 is configured to compare at least two input signals to generate an output signal. In an embodiment, the output signal may correspond to either "1" or "0." In an embodiment, the comparator 210 may generate output "1" if the value of a first signal (from the at least two signals) is greater than the value of a second signal (from the at least two signals). Similarly, the comparator 210 may generate an output "0" if the value of the first signal is less than the value of the second signal. In an embodiment, the comparator 210 may be realized through either software technologies or hardware technologies known in the art. Though, the comparator 210 is depicted as independent from the processor 202 in FIG. 1, a person skilled in the art would appreciate that the comparator 210 may be implemented within the processor 202 without departing from the scope of the disclosure.

Figure 3A:
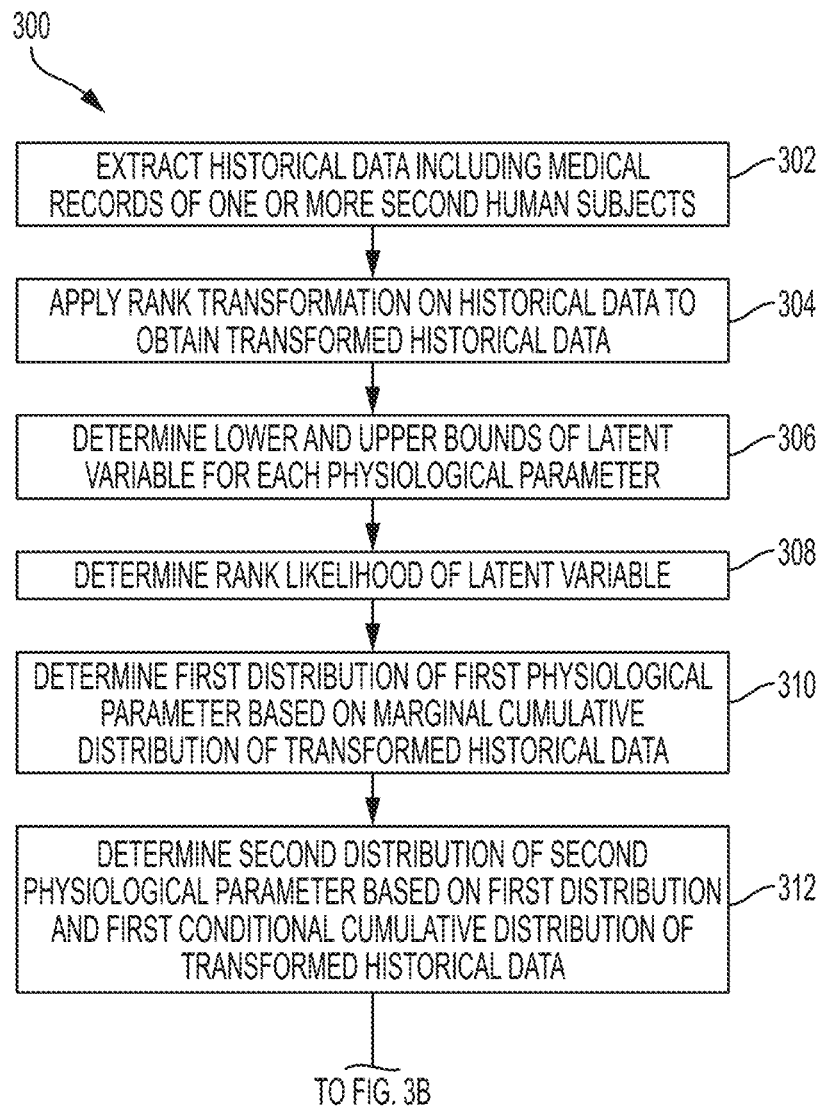
FIG. 3A and FIG. 3B illustrate a flowchart of a method for training a classifier based on a D-vine copula, in accordance with at least one embodiment.
Figure 3B:
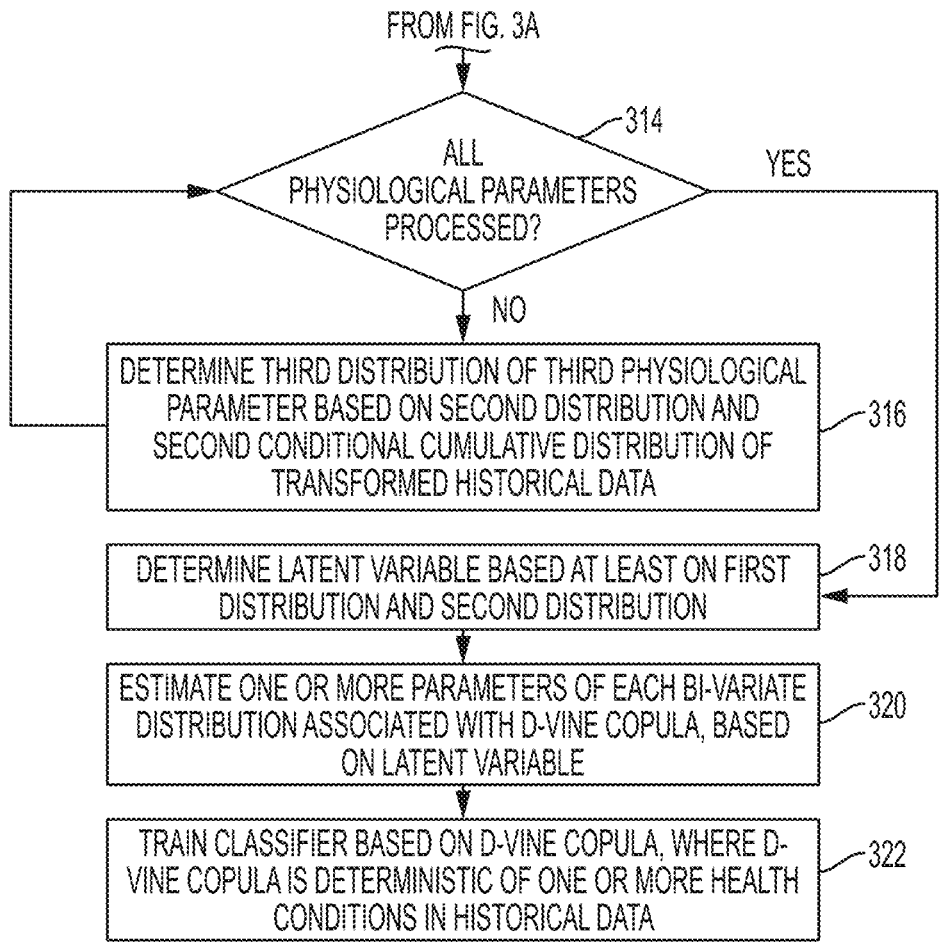

An embodiment of operation of the system 200 for training of a classifier based on a D-vine copula distribution has been explained further in conjunction with FIG. 3A and FIG. 3B. The prediction of a health condition of a first human subject using the trained classifier has been explained in conjunction with FIG. 4.

FIG. 3A and FIG. 3B illustrate a flowchart 300 of a method for training a classifier based on a D-vine copula, in accordance with at least one embodiment. The flowchart 300 has been described in conjunction with FIG. 1 and FIG. 2.

At step 302, a historical data including medical records of one or more second human subjects is extracted. In an embodiment, the processor 202 is configured to extract the historical data from the database server 104. In a scenario where the historical data is stored in the memory 204, the processor 202 may extract the historical data from the memory 204. In an embodiment, the historical data may correspond to a multivariate healthcare dataset, which includes a measure of one or more physiological parameters of each of the one or more second human subjects. Examples of the one or more physiological parameters include, but are not limited to, an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood hemoglobin level, and a blood platelet count. In an embodiment, the historical data may correspond to an m-dimensional multivariate dataset, where the one or more physiological parameters correspond to dimensions of the multivariate healthcare dataset. Thus, each physiological parameter may correspond to a different dimension in the m-dimensional multivariate dataset corresponding to the historical data. Further, each medical record in the historical data may correspond to an observation in the m-dimensional multivariate dataset corresponding to the historical data.

A person having ordinary skill in the art would understand that the scope of disclosure is not limited to the aforementioned physiological parameters. In an embodiment, various other physiological parameters may be used without departing from the spirit of the disclosure.

At step 304, a rank transformation is applied on the historical data to obtain a transformed historical data. In an embodiment, the processor 202 is configured to obtain the transformed historical data by applying the rank transformation on the historical data using an extended rank likelihood technique. To generate the transformed historical data, the processor 202 determines ranks of the individual observations in each of the p-dimensions in the historical data. In an embodiment, the processor 202 may assign a rank 1 to an observation having the highest value among the other observations in a particular dimension. Further, the processor 202 may assign a rank 2 to an observation having the next highest value in that dimension, and so on till a rank N to an observation having the lowest value in the particular dimension in the historical data. Thereafter, in an embodiment, the processor 202 may divide each rank by N so that the final values of the ranks of the observations lie between 0 and 1. The final values of the ranks of the observations, which lie between 0 and 1, may correspond to the transformed historical data. For example, the historical data includes five observations. The values of the five observations for a particular dimension may include the values 0.1, 5.6, 3.1, 0.8, and 2.2. The processor 202 may assign the ranks 1, 5, 4, 2, and 3 to the observations. Further, the processor 202 may determine the final values of the ranks, and hence the transformed historical data as 0.2, 1, 0.8, 0.4, and 0.6 (i.e., by dividing the ranks by 5).

A person skilled in the art will appreciate that the historical data may include data of various data types such as, but not limited to, a numerical data type or a categorical data type. However, in an embodiment, the transformed historical data may include only the ranks. Further, the transformed historical data may not have any missing values, even in a scenario where the historical data has certain missing values. In an embodiment, a bivariate copula distribution determined from the original historical data may be same as a bivariate copula distribution determined from the transformed historical data. As the transformed multivariate dataset does not include any missing values or categorical data, the bivariate copula distribution determined from the transformed historical data may be more accurate in identifying one or more clusters in the historical data (e.g., one or more health conditions of the second human subjects) than the bivariate copula distribution determined from the original historical data, which may have missing values or categorical data.

For example, the historical data includes a physiological parameter such as gender, which is of a categorical data type. Thus, observations for the physiological parameter "gender" may have either a value of "Male" or "Female", which may in turn be represented as "0" and "1" in the historical data. In an embodiment, the processor 202 may determine a binomial distribution of the observations of gender in the historical data. Thereafter, the processor 202 may fit the binomial distribution to a Gaussian distribution based on the rank transformation. Thus, the observations of categorical data type in the historical data may be converted into numerical data in the transformed historical data. Further, a missing value $u_{ij}$ in the historical data may be imputed based on an inverse transform sampling of a random variable $X_j$ (for the $j^{th}$ physiological parameter).

At step 306, a lower bound and an upper bound of a latent variable is determined for each physiological parameter from the one or more physiological parameters. In an embodiment, the latent variable may correspond to an intermediate variable, which may be determined from marginal distributions of the various physiological parameters in the historical data. In an embodiment, the latent variable may be used to determine one or more bivariate distributions of each pair of physiological parameters from the one or more physiological parameters.

In an embodiment, the processor 202 is configured to determine the lower bound (denoted by $U_{j,L}$) and the upper bound (denoted by $U_{j,H}$) of the latent variable (denoted by U) for a $j^{th}$ physiological parameter using the following equations:

$$U_{j,L} = \min\{u_{ij}: y_{ij} > y\} \quad (7)$$

$$U_{j,H} = \max\{u_{ij}: y_{ij} < y\} \quad (8)$$

where, $U_{j,L}$: the lower bound of the latent variable U for the $j^{th}$ physiological parameter;

$U_{j,H}$: the upper bound of the latent variable U for the $j^{th}$ physiological parameter;

y: each unique observation in the historical data, for a given value of the $j^{th}$ physiological parameter; and $y_{ij}$: $i^{th}$ observation of the $j^{th}$ physiological parameter in the historical data.

In an embodiment, the processor 202 may utilize the comparator 210 to perform the comparisons involved in the equations 7 and 8. For instance, the processor 202 may use the comparator 210 to compare a given value of $y_{ij}$ with y (i.e., each unique value of $y_{ij}$, for the $j^{th}$ physiological parameter).

At step 308, a rank likelihood of the latent variable is determined. In an embodiment, the processor 202 may be configured to determine the rank likelihood of the latent variable U. In an embodiment, to determine the rank likelihood of the latent variable U, based on the observations in the historical data (i.e., $y_{ij}$), the processor 202 may determine that values of the latent variable U may lie in a set H represented as under:

$$H_j = \{U_j \in R^n : \max\{u_{kj}: y_{kj} < y_{ij}\} < u_{ij} < \min\{u_{kj}: y_{ij} < y_{kj}\}\}, \quad \forall j \in [1, m] \quad (9)$$

where,

H: a set representing a range of values within which the latent variable U is constrained based on observations in the historical data (i.e., $y_{ij}$);

$u_{ij}$: the value of the latent variable U for the $i^{th}$ observation of the $j^{th}$ physiological parameter in the historical data;

$y_{ij}$: $i^{th}$ observation of the $j^{th}$ physiological parameter in the historical data;

n: number of observations in the historical data; and m: number of physiological parameters in the historical data.

In an embodiment, the processor 202 may determine the set H without a knowledge of univariate marginal distributions $F_i(X_i)$'s of the m-dimensional historical data. Thereafter, the processor 202 may determine the rank likelihood of the latent variable U as a probability of the latent variable U lying in the set H using the following equation:

$$P(U \in H | \Sigma, F_1, F_2, \ldots F_m) = \int_D P(U|\Sigma) dU = P(U \in H | \Sigma) \quad (10)$$

where, $\Sigma$: one or more parameters of a bivariate distribution (e.g., a bivariate copula distribution) associated with the historical data;

$F_1, F_2, \ldots F_m$: univariate marginal distributions of the m-dimensional historical data; and $P(U \in H | \Sigma)$: the rank likelihood of the latent variable U.

In an embodiment, the rank likelihood, the lower bound, and the upper bound of the latent variable may be utilized to determine the latent variable, as described further.

In order to determine the latent variable, at step 310, a first distribution of a first physiological parameter is determined. In an embodiment, the processor 202 is configured to determine the first distribution of the first physiological parameter based on a marginal cumulative distribution of the transformed historical data. In an embodiment, the processor 202 may use an inverse transform sampling technique to generate the first distribution. For instance, for the first physiological parameter, say p1, the processor 202 may generate a uniform random variable $U_{i,p1}$ and transform the uniform random variable $U_{i,p1}$ using an inverse of the marginal cumulative distribution of the transformed historical data $CDF^{-1}(RT(F_i(X_i)))$, where RT: rank transformation. Thereafter, based on the transforming of the uniform random variable $U_{i,p1}$, the processor 202 may generate samples of the first distribution, say $U_{p1}$, thereby determining the first distribution $U_{p1}$. In an embodiment, the processor 202 may truncate the first distribution based on a lower bound and an upper bound of the latent variable for the first physiological parameter. The following expression denotes the determination of the first distribution:

$$U_{p1} \sim \text{unif}(U_{p1,L}, U_{p1,H}) \quad (11)$$

where, $U_{p1}$: the first distribution of the first physiological parameter p1;

$U_{p1,L}$: the lower bound of the latent variable U for the first physiological parameter p1;

$U_{p1,H}$: the upper bound of the latent variable U for the first physiological parameter p1; and unif( ): uniform distribution function.

A person skilled in the art will understand that the first distribution may correspond to a marginal cumulative distribution of the first physiological parameter.

At step 312, a second distribution of a second physiological parameter is determined. In an embodiment, the processor 202 is configured to determine the second distribution of the second physiological parameter based at least on the first distribution and a first conditional cumulative distribution of the transformed historical data. In an embodiment, the first conditional cumulative distribution may be deterministic of at least a relation between the first physiological parameter and the second physiological parameter. For instance, for the second physiological parameter, say p2, the processor 202 may determine the first conditional cumulative distribution of the transformed historical data, represented by $F(U_{p2}|U_{p1})$. In an embodiment, the processor 202 may determine the first conditional cumulative distribution $F(U_{p2}|U_{p1})$ by determining a corresponding h-function $h(U_{p2}, U_{p1})$ using one or more mathematical or statistical techniques known in the art. Further, in an embodiment, the processor 202 may truncate the first conditional cumulative distribution with respect to the upper bound and the lower bound of the latent variable for the second physiological parameter. The following expression denotes the truncation of the first conditional cumulative distribution:

$$R_{p2} \sim \text{unif}(R_{p2,L}, R_{p2,H}) \quad (12)$$

where, $R_{p2}$: the truncated first conditional cumulative distribution;

$R_{p2,L}$: the lower bound for truncation of the first conditional cumulative distribution, where $R_{p2,L} = F(U_{p2,L}|U_{p1})$, and $U_{p2,L}$: lower bound of the latent variable U for p2;

$R_{p2,H}$: the upper bound for truncation of the first conditional cumulative distribution, where $R_{p2,H}=F(U_{p2,H}|U_{p1})$, and $U_{p2,H}$: upper bound of the latent variable U for p2; and unif( ): uniform distribution function.

After determining the truncated first conditional cumulative distribution, i.e., $R_{p2}$, in an embodiment, the processor 202 may determine the second distribution of the second physiological parameter p2, i.e., $U_{p2}$, by inverting the h-function $h(U_{p2}, U_{p1})$ with respect to $U_{p2}$. In an embodiment, the following expression denotes the determination of the second distribution:

$$R_{p2}=h(U_{p2},U_{p1}) \Rightarrow U_{p2}=h^{-1}(R_{p2},U_{p1}) \qquad (13)$$

where, $U_{p2}$: the second distribution of the second physiological parameter p2.

A person skilled in the art will understand that as the second distribution is determined from the truncated first conditional cumulative distribution; the second distribution may also in turn be truncated within the lower and the upper bounds of the latent variable U for the second physiological parameter.

Further, a person skilled in the art will understand that the second distribution may correspond to a marginal cumulative distribution of the second physiological parameter.

At step 314, a check is performed to determine whether all physiological parameters in the historical data have been processed. In an embodiment, the processor 202 is configured to perform the check using the comparator 210. If there exists another physiological parameter that has not been processed yet, the processor 202 performs step 316. Otherwise, the processor 202 may perform step 318.

At step 316, a third distribution of a third physiological parameter is determined. In an embodiment, the processor 202 is configured to determine the third distribution of the third physiological parameter based on the second distribution and a second conditional cumulative distribution of the transformed historical data. In an embodiment, the second conditional cumulative distribution may be deterministic of at least a relation between the third physiological parameter and one or more of the first physiological parameter and the second physiological parameter. For instance, for the third physiological parameter, say p3, the processor 202 may determine the second conditional cumulative distribution of the transformed historical data, represented by $F(U_{p3}|U_{p1}, U_{p2})$. In an embodiment, the processor 202 may determine the second conditional cumulative distribution $F(U_{p3}|U_{p1}, U_{p2})$ by determining a corresponding h-function $h(F(U_{p3}|U_{p2}), F(U_{p1}|U_{p2}))$ using one or more mathematical or statistical techniques known in the art. Further, in an embodiment, the processor 202 may truncate the second conditional cumulative distribution with respect to the upper bound and the lower bound of the latent variable for the third physiological parameter. The truncation of the second conditional cumulative distribution may be performed in a manner similar to the truncation of the first conditional cumulative distribution, as denoted in expression 12.

After determining the truncated second conditional cumulative distribution, say, $R_{p3}$, in an embodiment, the processor 202 may determine the third distribution of the third physiological parameter p3, i.e., $U_{p3}$, by recursively inverting the h-function $h(F(U_{p3}|U_{p2}), F(U_{p1}|U_{p2}))$ with respect to its first argument at each iteration. In an embodiment, the following expression denotes the determination of the third distribution:

$$R_{p3}=h(U_{p3}|U_{p2}),F(U_{p1}|U_{p2})) \Rightarrow R_{p3}=h^{-1}(R_{p3},F(U_{p1}|U_{p2})) \Rightarrow U_{p3}=h^{-1}(R_{p3},U_{p2}) \qquad (14)$$

where, $R_{p3}$: the truncated second conditional cumulative distribution; and $U_{p3}$: the third distribution of the third physiological parameter p3.

A person skilled in the art will understand that as the third distribution is determined from the truncated second conditional cumulative distribution; the third distribution may also in turn be truncated within the lower and the upper bounds of the latent variable U for the third physiological parameter.

Further, a person skilled in the art will understand that the third distribution may correspond to a marginal cumulative distribution of the third physiological parameter.

In an embodiment, the processor 202 may continue to iterate the steps 314 and 316 until all physiological parameters in the historical data are processed. In an embodiment, for a $j^{th}$ physiological parameter $p_j$, the processor 202 may determine a conditional cumulative distribution $F(U_{pj}|U_{p1}, \ldots U_{pj-1})$ using a corresponding h-function $h(F(U_{pj}|U_{p2}, \ldots U_{pj-1}), F(U_{p1}|U_{p2}, \ldots U_{pj-1}))$. Thereafter, the processor 202 may truncate the conditional cumulative distribution based on the lower and the upper bounds of the latent variable U for the $j^{th}$ physiological parameter $p_j$, in a manner similar to that described above. Further, the processor 202 may determine a distribution of the $j^{th}$ physiological parameter pj, i.e., $U_{pj}$, by recursively inverting the h-function $h(F(U_{pj}|U_{p2}, \ldots U_{pj-1}), F(U_{p1}|U_{p2}, \ldots U_{pj-1}))$ with respect to its first argument at each iteration. In an embodiment, the distribution, so determined, may correspond to a marginal cumulative distribution of the $j^{th}$ physiological parameter. In an embodiment, the following expression denotes the determination of the distribution $U_{pj}$:

$$R_{pj}=h(F(U_{pj}|U_{p2}, \ldots U_{pj-1}),F(U_{p1}|U_{p2}, \ldots U_{pj-1}))$$
$$\text{for } t \text{ in } 2{:}j{-}1 do \Rightarrow R_{pj}=h^{-1}(R_{pj},F(U_{pt-1}|U_{pt}, \ldots U_{pj-1})) \Rightarrow U_{pj}=h^{-1}(R_{pj},U_{pj-1}) \qquad (15)$$

where, $R_{pj}$: truncated conditional cumulative distribution for the $j^{th}$ physiological parameter $p_j$;

$U_{pj}$: distribution of the $j^{th}$ physiological parameter $p_j$; and $U_{pj-1}$: distribution of the $(j-1)^{th}$ physiological parameter where $U_{pj-1}$ may be determined in a preceding iteration of the step 314.

At step 318, the latent variable is determined. In an embodiment, the processor 202 is configured to determine the latent variable based at least on the first distribution and the second distribution. In an embodiment, the processor 202 may determine the latent variable based on the marginal cumulative distributions (e.g., $U_i=F_i(X_i)$) of the one or more physiological parameters (e.g., a physiological parameter sampled using a random variable $X_i$), as determined in the steps 310 through 316. To determine the latent variable, the processor 202 may aggregate the marginal cumulative distributions into an n*m matrix, where n: number of observations of each physiological parameter, and m: number of physiological parameters. For instance, the historical data includes four physiological parameters p1, p2, p3, and p4. In such a scenario, the processor 202 may determine the corresponding marginal cumulative distributions of each of the four physiological parameters, say, $U_{p1}$, $U_{p2}$, $U_{p3}$, and $U_{p4}$, in a manner similar to that described above in the steps 310 through 316. In an embodiment, the processor 202 may determine the latent variable U as an n*4 matrix including the individual distributions, for example, $U=[U_{p1}, U_{p2}, U_{p3}, U_{p4}]$.

In an embodiment, the latent variable may be utilizable to determine one or more parameters of each of one or more bivariate distributions associated with a D-vine copula. In an embodiment, the D-vine copula may correspond to a hierarchal structure representing the one or more bivariate distributions of the D-vine copula. The D-vine copula may be represented graphically by a set of hierarchal trees, each of which may include a set of nodes arranged sequentially and connected by a set of edges. Further, each edge, connecting a pair of nodes in a hierarchal tree, may represent a bivariate copula distribution. In an embodiment, the D-vine copula may model a dependency between each pair of physiological parameters in the historical data. An example D-vine copula has been explained in conjunction with FIG. 5.

At step 320, one or more parameters of each of the one or more bivariate distributions associated with the D-vine copula are estimated. In an embodiment, the processor 202 is configured to estimate the one or more parameters of each of the one or more bivariate distributions using one of a Gibbs sampling technique or an Expectation Maximization (EM) technique. In an embodiment, the one or more bivariate distributions may correspond to a bivariate copula distribution including, but not limited to, a T-student copula distribution, a Clayton copula distribution, a Gumbel copula distribution, and a Gaussian copula distribution. In a scenario where a bivariate distribution is a bivariate Gaussian copula distribution, in an embodiment, the one or more parameters of the bivariate distribution may include at least a covariance matrix associated with the bivariate Guassian copula distribution.

To estimate the one or more parameters of each of the one or more bivariate distributions, the processor 202 may create a matrix W (n*2 matrix) based on the latent variable U. To create the matrix W, the processor 202 may first determine a hierarchal level of the bivariate copula distribution within the hierarchal representation of the D-vine copula. In an embodiment, if the bivariate copula distribution is represented at the first level in the D-vine copula, the processor 202 may assign the matrix W with the corresponding distributions of the pair physiological parameters related to the bivariate copula distribution. Alternatively, if the bivariate copula distribution is represented at a higher level in the D-vine copula (other than the first level), the processor 202 may assign the matrix W with the pair of conditional cumulative distributions related to the bivariate copula distribution. In an embodiment, the pair of conditional cumulative distributions may be determined using corresponding h-functions, in a manner similar to that described above. The assignment of the values to the n*2 matrix W may be represented as follows:

$$\text{if } (j=1) \Rightarrow W=[U_l, U_{l+j}] \quad (16)$$

$$\text{if } (i>1) \Rightarrow W=[U_{l|l+1, \ldots, l+j-1}, U_{l+j|l+1, \ldots, l+j-1}] \quad (17)$$

where,
j: hierarchal level of the bivariate copula distribution in the D-vine copula;
l: position of the edge representing the bivariate copula distribution within the hierarchal level j;
$U_j$: distribution of the $j^{th}$ physiological parameter;
$U_{l+j}$: distribution of the $(l+j)^{th}$ physiological parameter;
$U_{l|l+1, \ldots, l+j-1}$: conditional cumulative distribution for the $l^{th}$ physiological parameter, where $U_{l|l+1, \ldots, l+j-1}$=$F(U_l|U_{l+1}, \ldots, U_{l+j-1})$; and $U_{l+j|l+1, \ldots, l+j-1}$: conditional cumulative distribution for the $l^{th}$ physiological parameter, where $U_{l+j|l+1, \ldots, l+j-1}$=$F(U_{l+j}|U_{l+1}, \ldots, U_{l+j-1})$.

After assigning values to the n*2 matrix W, in an embodiment, the processor 202 may determine the one or more parameters of the bivariate distribution based on an inverse Wishart distribution, parameterized based on the latent variable. The following expression denotes the determination of the one or more parameters of the bivariate distribution:

$$\Sigma_{l,j+1|l+1, \ldots, l+j-1} \sim \text{Inverse-Wishart}(v_0+n, v_0V_0+W^T \cdot W) \quad (18)$$

where,
$\Sigma_{l,j+1|l+1, \ldots, l+j-1}$: one or more parameters of the bivariate copula $C_{l,l+j|l+1, \ldots, l+j-1}$;
n: number of observations in the historical data
$v_0, V_0$: configurable parameters of the inverse Wishart distribution; and
Inverse-Wishart( ): inverse Wishart distribution.

A person skilled in the art will understand that the scope of the disclosure should not be limited to estimating the one or more parameters of each bivariate distribution associated with the D-vine copula, as discussed above. Various other statistical techniques known in the art may be used to estimate the one or more parameters without departing from the scope of the disclosure.

At step 322, a classifier is trained based on the D-vine copula distribution. In an embodiment, the processor 202 is configured to train the classifier. In an embodiment, the processor 202 may determine each bivariate copula distribution associated with the D-vine copula based on the respective one or more parameters of the bivariate copula distributions, as discussed above. Further, as discussed, the one or more bivariate copula distributions associated with the D-vine copula may be deterministic of the one or more health conditions of the one or more second human subjects in the historical data. In an embodiment, the processor 202 may train the classifier based on the bivariate copula distributions associated with the D-vine copula and the historical data, using one or more machine learning techniques known in the art. Examples of the classifier may include, but are not limited to, a Support Vector Machine (SVM), a Logistic Regression, a Bayesian Classifier, a Decision Tree Classifier, a Copula-based Classifier, a K-Nearest Neighbors (KNN) Classifier, or a Random Forest (RF) Classifier.

A person skilled in the art would appreciate that the scope of the disclosure is not limited to the training of the classifier, as discussed above. The classifier may be trained using any machine learning or artificial intelligence technique known in the art without departing from the spirit of the disclosure.

Figure 4:
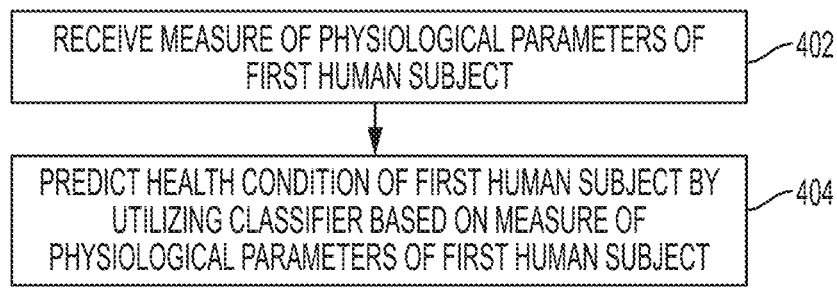
FIG. 4 illustrates a flowchart of a method for predicting a health condition of a first human subject, in accordance with at least one embodiment.

FIG. 4 illustrates a flowchart 400 of a method for predicting a health condition of a first human subject, in accordance with at least one embodiment.

At step 402, a measure of the one or more physiological parameters of a first human subject is received. In an embodiment, the processor 202 is configured to receive the measure of the one or more physiological parameters of the first human subject from the human subject-computing device 106 of the first human subject. In an embodiment, as discussed, the one or more biosensors, for example, 108a, may be inbuilt within the human subject-computing device 106. Alternatively, the one or more biosensors, for example, 108a may be coupled to the human subject-computing device 106 through the one or more DAQ interfaces, for example, 110a. In an embodiment, the one or more biosensors, for example, 108a, may measure the one or more physiological parameters of the first human subject. Thereafter, the human subject-computing device 106 may send the one or more physiological parameters of the first human subject to the processor 202.

At step 404, the health condition of the first human subject is predicted using the classifier. In an embodiment, the processor 202 is configured to predict the health condition of the first human subject using the classifier. Prior to predicting the health condition, the processor 202 may receive a measure of the one or more physiological parameters of the first human subject from the user. Based on the one or more physiological parameters of the first human subject, the processor 202 may predict the health condition of the first human subject by utilizing the classifier. Further, the processor 202 may display the predicted health condition of the first human subject through a user-interface on the human subject-computing device 106 of the first human subject. In an embodiment, the health condition may correspond to at least one of a disease risk, a disease symptom, an onset of a disease, a recovery from a disease, or an effect of medications for a disease.

A person having ordinary skill in the art would understand that the scope of the disclosure should not be limited to determining a health condition of a human subject. In an embodiment, similar medical data may be analyzed to draw out various inferences. For instance, insurance data pertaining to health care may be analyzed to determine health insurance frauds.

Further, the disclosure may be implemented for analysis of data from various levels of the healthcare industry such as at individual patient level through analysis of Electronic Medical Records (EMR), or at hospital level (e.g., identifying a group of patients having risk of getting involved in health insurance frauds). For example, the historical data may correspond to a multivariate dataset including medical insurance records of one or more individuals. In such a scenario, the p-dimensional variable in each medical insurance record may correspond to one or more insurance related parameters such as age of an insured person, one or more physiological parameters of the insured person, premium being paid by the insured person, insurance amount, coverage limit, and so on. Thus, the process described in the flowchart 300 may be utilized to determine insurance frauds, recommend insurance amounts, etc.

Further, a person skilled in the art would appreciate that the scope of the disclosure should not be limited to predicting the health condition of the first human subject. In an embodiment, the disclosure may be implemented for identifying one or more categories in any multivariate dataset. Further, the disclosure may be implemented for predicting a category from the one or more categories into which a new record of the multivariate dataset may classified. For example, the disclosure may be implemented to analyze a financial dataset to determine a credit risk category of a customer. Further, the financial dataset may be analysed to categorize the customers in one or more categories of buying behaviors. The financial dataset may include various types of financial data such as, but not limited to, loan risk assessment data, insurance data, bank statements, and bank transaction data.

Figure 5:
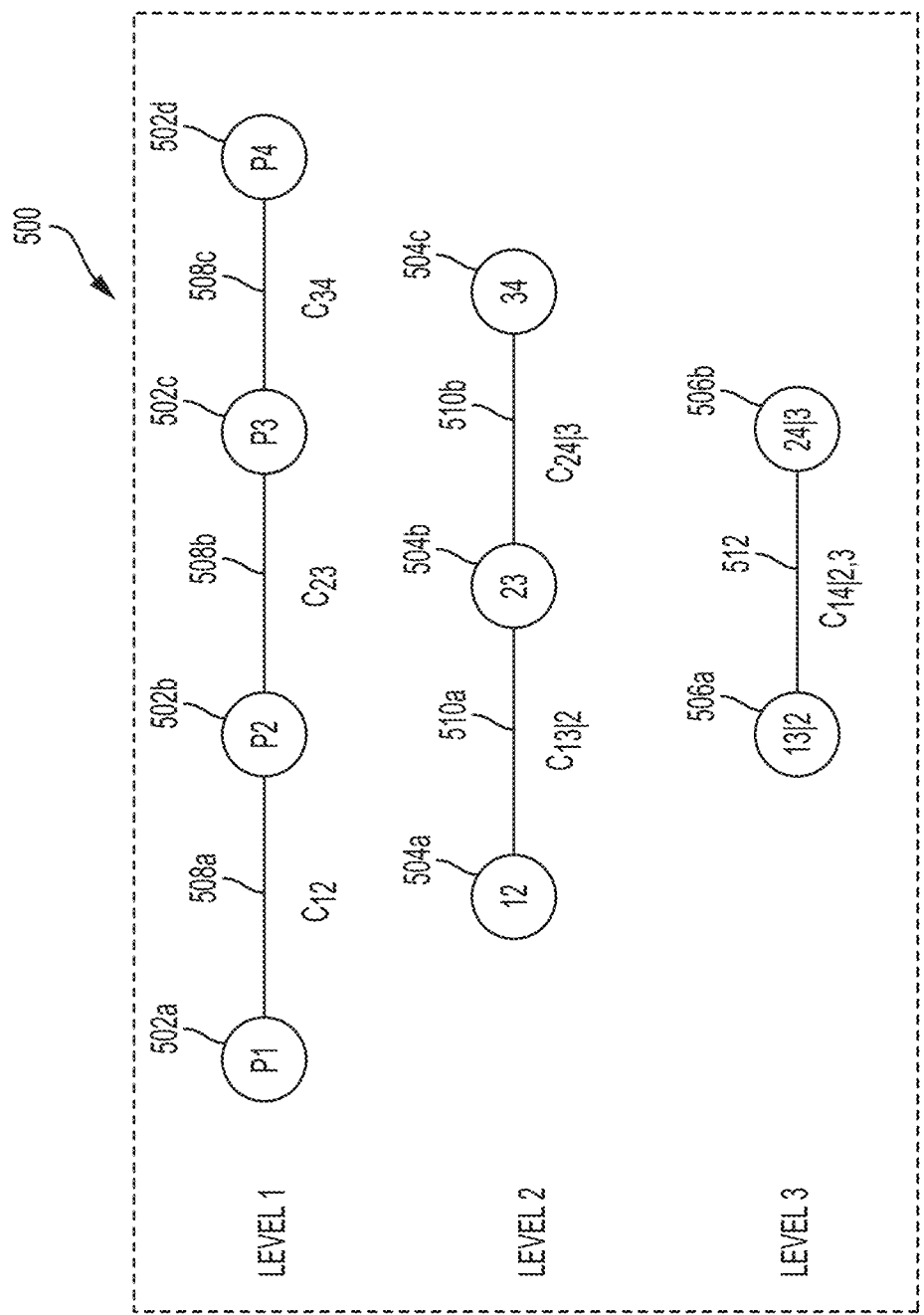
FIG. 5 illustrates an example D-vine copula distribution model, in accordance with at least one embodiment.

FIG. 5 illustrates an example D-vine copula distribution model 500, in accordance with at least one embodiment.

In an embodiment, the D-vine copula 500 of FIG. 5 corresponds to a scenario in which the multivariate historical data includes four physiological parameters, for example, P1, P2, P3, and P4. Thus, as shown in FIG. 5, the D-vine copula 500 may include three hierarchal trees (i.e., m−1 hierarchal tree, where m: number of physiological parameters). A hierarchal tree at a particular level of the D-vine copula 500 may include a sequence of connected nodes. In an embodiment, the tree at the first level of the D-vine copula 500 may represent the various physiological parameters in the multivariate historical data. Thus, the number of nodes at the first level may be same as the number of the physiological parameters. Further, the tree at the first level may represent bivariate copula distributions between pairs of physiological parameters. In an embodiment, the tree at each subsequent level may represent bivariate copula distributions of the preceding level and conditional bivariate copula distributions determined based on such bivariate copula distributions of the preceding level.

For instance, the tree at the level 1 of the D-vine copula 500 includes four nodes 502a-502d representing the four physiological parameters P1, P2, P3, and P4 respectively. The nodes 502a-502d are sequentially connected by edges 508a-508c, where each edge represents a bivariate copula distribution between the respective physiological parameters. For example, as shown in FIG. 5, the edge 508a connects the node 502a (representing P1) and the node 502b (representing P2). Thus, the edge 508a may represent the bivariate copula $C_{12}$. Similarly, the edge 508b, connecting the nodes 502b and 502c (representing the physiological parameters P2 and P3, respectively), may represent of the bivariate copula $C_{23}$, and so on.

Further, the tree at the level 2 of the D-vine copula 500 includes three nodes 504a-504c. Each of the three nodes (i.e., 504a-504c) may represent a corresponding bivariate copula represented at the previous level. For instance, as shown in FIG. 5, the node 504a at the level 2 may correspond to the edge 508a of the level 1. Similarly, the node 504b at the level 2 may correspond to the edge 508b of the level 1, and so on. Hence, the node 504a may denote the bivariate copula $C_{12}$, which is represented by the corresponding edge 508a of the previous level, i.e., the level 1. Similarly, the node 504b may denote the bivariate copula $C_{23}$, which is represented by the corresponding edge 508b of the level 1, and so on.

Further, the nodes 504a-504c, at the level 2 of the D-vine copula 500, may be sequentially connected by edges 510a and 510b, respectively. Each edge between a pair of nodes at the level 2 may represent a conditional bivariate copula, which may be determined based on the pair of bivariate copulas, represented by the pair of nodes. For instance, the edge 510a connects the node 504a (representing $C_{12}$) and node 504b (representing $C_{23}$). Thus, the edge 510a may represent the conditional bivariate copula $C_{13|2}$. Similarly, the edge 510b, connecting the nodes 504b and 504c (representing $C_{23}$ and $C_{34}$, respectively), may represent the conditional bivariate copula $C_{24|3}$.

In addition, the tree at the level 3 of the D-vine copula 500 includes two nodes 506a and 506b. The node 506a may correspond to the edge 510a of the previous level, i.e., the level 2. Further, the node 506b may correspond to the edge 510b of the level 2. Hence, the node 506a may denote the conditional bivariate copula $C_{13|2}$, which is represented by the corresponding edge 510a. Similarly, the node 506b may denote the conditional bivariate copula $C_{24|3}$, which is represented by the corresponding edge 510b. Further, the nodes 506a and 506b may be connected by an edge 512. The edge 512 may represent the conditional bivariate copula $C_{14|3,2}$, which may be determined based on the conditional bivariate copulas $C_{13|2}$ and $C_{24|3}$ (denoted by the nodes 506a and 506b respectively).

A person skilled in the art will understand that though the D-vine copula 500 has been illustrated for an example scenario of four physiological parameters, the D-vine copula 500 may be similarly extended for any number of physiological parameters. In an embodiment, the number of levels of the D-vine copula 500 may be given by m−1 and the number of bivariate copulas represented by the D-vine copula 500 may be given by m(m−1)/2, where m: number of physiological parameters.

Further, in an embodiment, the individual bivariate copulas in the D-vine copula 500 may include, but are not limited to, a T-student copula distribution, a Clayton copula distribution, a Gumbel copula distribution, or a Gaussian copula distribution.

Figure 6A:
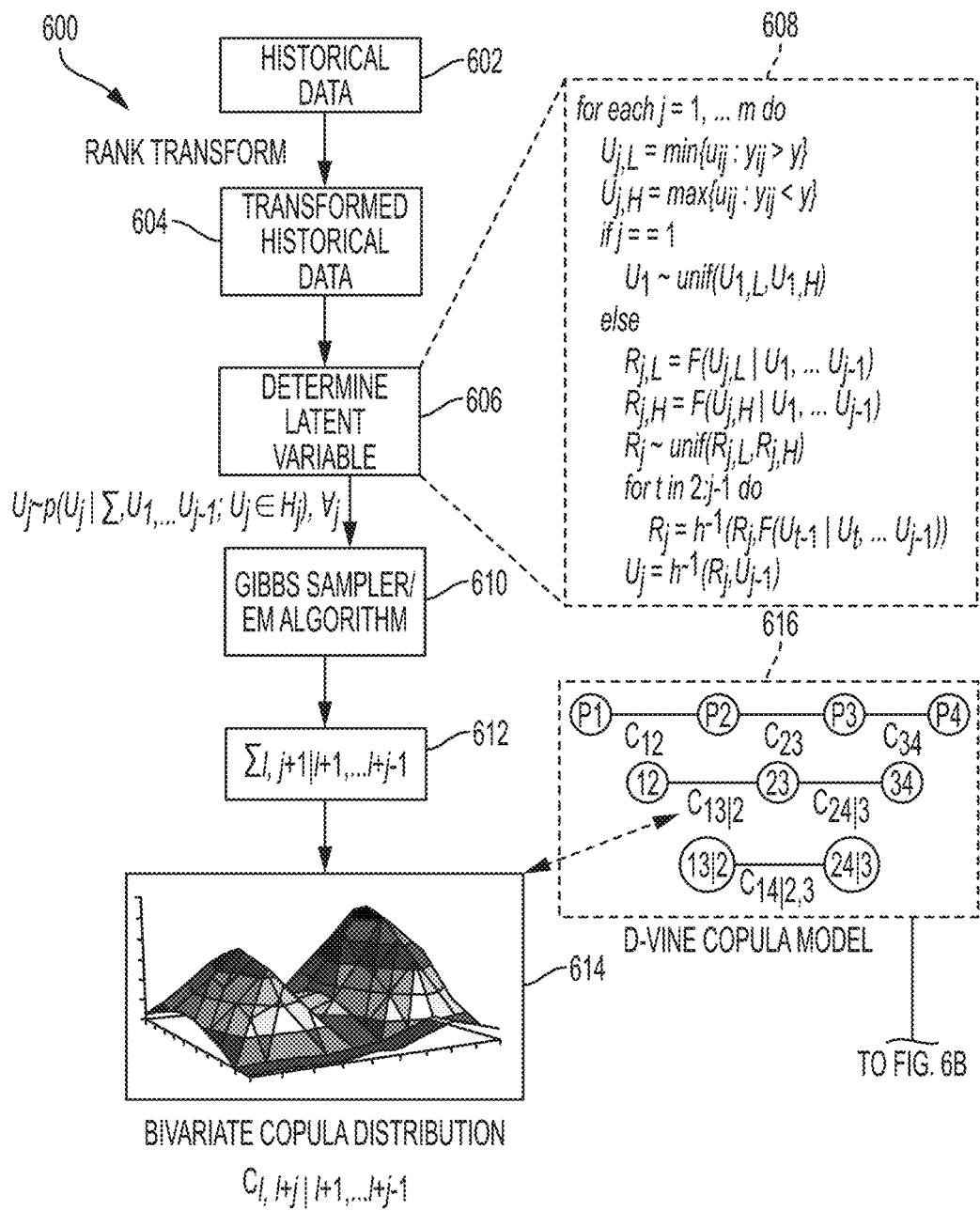
FIG. 6A and FIG. 6B illustrate a flow diagram of a method for predicting a health condition of a first human subject, in accordance with at least one embodiment.
Figure 6B:
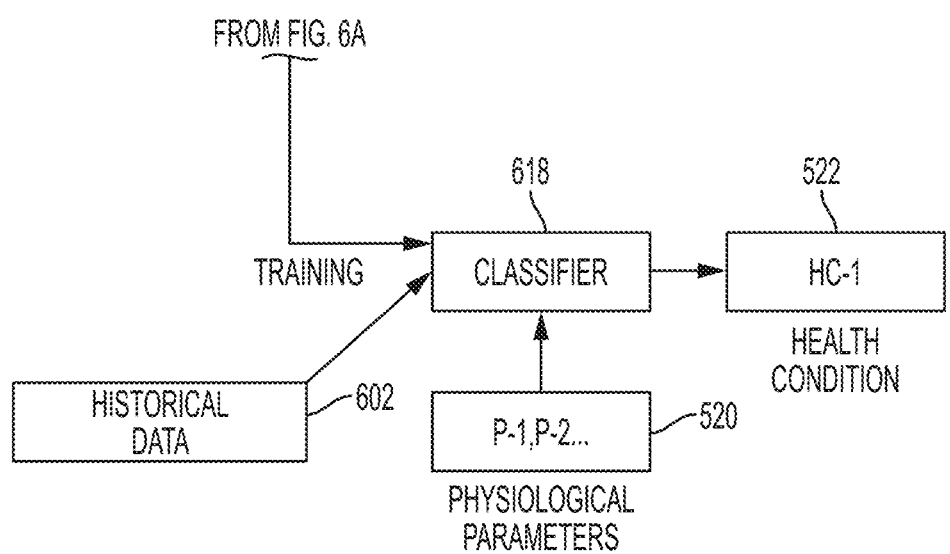

FIG. 6A and FIG. 6B illustrate a flow diagram 600 of method for predicting the health condition of the first human subject, in accordance with at least one embodiment. The flow diagram 600 has been described in conjunction with FIG. 1, FIG. 2, FIG. 3A, FIG. 3B, and FIG. 4.

As shown in FIG. 6A and FIG. 6B, the processor 202 receives the historical data (depicted by 602) including the medical records of the one or more second human subjects. In an embodiment, the processor 202 may retrieve the historical data (depicted by 602) from a database or receive the historical data (depicted by 602) from the user, as described in the step 302 (FIG. 3A). Thereafter, the processor 202 may apply the rank transformation on the historical data (depicted by 602) to obtain the transformed historical data (depicted by 604), in manner similar to that disclosed in the step 304 (FIG. 3A). Further, the processor 202 determines the latent variable U (depicted by 606), in manner similar to that disclosed in the steps 306 through 318 (FIG. 3B). In an embodiment, the determination of the latent variable U may be represented by the following expression:

$$U_j \sim p(U_j|\Sigma, U_1, \ldots U_{j-1}; U_j \in H_j), \forall j \in [1, m] \quad (19)$$

As shown in FIG. 5, a pseudo-code 608 illustrates the determination of the latent variable U in detail. The pseudo-code 608 is represented as under:

1. for each j=1, . . . m do
2. $U_{j,L} = \min\{u_{ij} : y_{ij} > y\}$
3. $U_{j,H} = \max\{u_{ij} : y_{ij} < y\}$
4. if j=1
5. $U_1 \sim \text{unif}(U_{1,L}, U_{1,H})$
6. else
7. $R_{j,L} = F(U_{j,L}|U_1, \ldots U_{j-1})$
8. $R_{j,H} = F(U_{j,H}|U_1, \ldots U_{j-1})$
9. $R_j \sim \text{unif}(R_{j,L}, R_{j,H})$
10. for t in 2:j−1 do
11. $R_j = h^{-1}(R_j, F(U_{t-1}|U_t, \ldots U_{j-1}))$
12. $U_j = h^{-1}(R_j, U_{j-1})$ Thereafter, the processor 202 may estimate the one or more parameters (depicted by 612) of each of the one or more bivariate distributions (depicted by 614) associated with a D-vine copula (depicted by 616). For example, a covariance matrix $\Sigma_{l,j+1|l+1, \ldots l+j-1}$ of each bivariate copula distribution $C_{l,j+1|l+1, \ldots l+j-1}$. In an embodiment, the processor 202 may use a Gibbs Sampler/EM Algorithm (depicted by 610) to estimate the one or more parameters (depicted by 612), in a manner similar to that discussed in the step 320 (FIG. 3B). Based on the estimated one or more parameters of each bivariate distribution (depicted by 612), in an embodiment, the processor 202 may determine the respective bivariate distributions (e.g., the bivariate copula distribution $C_{l,j+1|l+1, \ldots l+j-1}$, depicted by 614). In an embodiment, the processor 202 may determine the various bivariate copula distributions of the D-vine copula distribution model (depicted by 616), in a manner similar to that described above.

Thereafter, based at least on the various bivariate copula distributions associated with the D-vine copula (depicted by 616) and the historical data 602, the processor 202 may train a classifier 618, using one or more machine learning techniques known in the art, as explained in the step 322 (FIG. 3B). Further, the processor 202 may receive a measure of the one or more physiological parameters (such as, physiological parameters P-1, P-2 . . . depicted by 520) of the first human subject from the human subject-computing device 106, as explained in the step 402 (FIG. 4). The processor 202 may use the classifier (depicted by 618) to predict the health condition (e.g., the health condition HC-1, depicted by 522) of the first human subject based on the one or more physiological parameters (depicted by 520) of the first human subject, as explained in the step 404 (FIG. 4).

The disclosed embodiments encompass numerous advantages. The disclosure leads to an effective clustering of a multivariate dataset using a D-vine copula distribution model. For example, the multivariate dataset may be a healthcare dataset that includes medical records of one or more human subjects. By using the D-vine copula, one or more clusters indicative of one or more health conditions of the one or more human subjects may be identified. The D-vine copula, though a very robust statistical method for clustering data of a numerical data type, may be inefficient while handling data of a categorical data type. Further, the D-vine copula may not perform well in case of missing values in the multivariate dataset. In addition, the sampling of latent variables for determining the D-vine copula may be a non-trivial task. The disclosure overcomes the aforementioned shortcomings of the D-vine copula for clustering the multivariate dataset and determination of complex dependencies within the multivariate dataset.

The disclosed methods and systems, as illustrated in the ongoing description or any of its components, may be embodied in the form of a computer system. Typical examples of a computer system include a general-purpose computer, a programmed microprocessor, a micro-controller, a peripheral integrated circuit element, and other devices or arrangements of devices that are capable of implementing the steps that constitute the method of the disclosure.

The computer system comprises a computer, an input device, a display unit and the Internet. The computer further comprises a microprocessor. The microprocessor is connected to a communication bus. The computer also includes a memory. The memory may be Random Access Memory (RAM) or Read Only Memory (ROM). The computer system further comprises a storage device, which may be a hard-disk drive or a removable storage drive, such as, a floppy-disk drive, optical-disk drive, and the like. The storage device may also be a means for loading computer programs or other instructions into the computer system. The computer system also includes a communication unit. The communication unit allows the computer to connect to other databases and the Internet through an input/output (I/O) interface, allowing the transfer as well as reception of data from other sources. The communication unit may include a modem, an Ethernet card, or other similar devices, which enable the computer system to connect to databases and networks, such as, LAN, MAN, WAN, and the Internet. The computer system facilitates input from a user through input devices accessible to the system through an I/O interface.

In order to process input data, the computer system executes a set of instructions that are stored in one or more storage elements. The storage elements may also hold data or other information, as desired. The storage element may be in the form of an information source or a physical memory element present in the processing machine.

The programmable or computer-readable instructions may include various commands that instruct the processing machine to perform specific tasks, such as steps that constitute the method of the disclosure. The systems and methods described can also be implemented using only software programming or using only hardware or by a varying combination of the two techniques. The disclosure is independent of the programming language and the operating system used in the computers. The instructions for the disclosure can be written in all programming languages including, but not limited to, "C," "C++," "Visual C++" and "Visual Basic." Further, the software may be in the form of a collection of separate programs, a program module containing a larger program or a portion of a program module, as discussed in the ongoing description. The software may also include modular programming in the form of object-oriented programming. The processing of input data by the processing machine may be in response to user commands, the results of previous processing, or from a request made by another processing machine. The disclosure can also be implemented in various operating systems and platforms including, but not limited to, "Unix," "DOS," "Android," "Symbian," and "Linux."

The programmable instructions can be stored and transmitted on a computer-readable medium. The disclosure can also be embodied in a computer program product comprising a computer-readable medium, or with any product capable of implementing the above methods and systems, or the numerous possible variations thereof.

Various embodiments of methods and systems for predicting health condition of a human subject have been disclosed. However, it should be apparent to those skilled in the art that modifications in addition to those described, are possible without departing from the inventive concepts herein. The embodiments, therefore, are not restrictive, except in the spirit of the disclosure. Moreover, in interpreting the disclosure, all terms should be understood in the broadest possible manner consistent with the context. In particular, the terms "comprises" and "comprising" should be interpreted as referring to elements, components, or steps, in a non-exclusive manner, indicating that the referenced elements, components, or steps may be present, or utilized, or combined with other elements, components, or steps that are not expressly referenced.

A person having ordinary skills in the art will appreciate that the system, modules, and sub-modules have been illustrated and explained to serve as examples and should not be considered limiting in any manner. It will be further appreciated that the variants of the above disclosed system elements, or modules and other features and functions, or alternatives thereof, may be combined to create other different systems or applications.

Those skilled in the art will appreciate that any of the aforementioned steps and/or system modules may be suitably replaced, reordered, or removed, and additional steps and/or system modules may be inserted, depending on the needs of a particular application. In addition, the systems of the aforementioned embodiments may be implemented using a wide variety of suitable processes and system modules and is not limited to any particular computer hardware, software, middleware, firmware, microcode, or the like.

The claims can encompass embodiments for hardware, software, or a combination thereof.

It will be appreciated that variants of the above disclosed, and other features and functions or alternatives thereof, may be combined into many other different systems or applications. Presently unforeseen or unanticipated alternatives, modifications, variations, or improvements therein may be subsequently made by those skilled in the art, which are also intended to be encompassed by the following claims.

What is claimed is:

1. A method of operating a health condition profiling system, the method comprising:

receiving, by a transceiver, a measure of one or more physiological parameters associated with a first human subject, wherein said one or more physiological parameters comprise at least one of an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood haemoglobin level, and a blood platelet count;

extracting, by one or more processors, a historical data comprising a measure of said one or more physiological parameters associated with each of one or more second human subjects, wherein the historical data is missing values, comprises categorical data, or both;

determining, by said one or more processors, a first distribution associated with a first physiological parameter, from said one or more physiological parameters, based on a marginal cumulative distribution of a transformed historical data, wherein said transformed historical data is determined by ranking of said historical data, and does not include any missing values or categorical data;

determining, by said one or more processors, a second distribution associated with a second physiological parameter, from said one or more physiological parameters, based on said first distribution and a first conditional cumulative distribution of said transformed historical data, wherein said first conditional cumulative distribution is deterministic of at least an association between said first physiological parameter and said second physiological parameter;

determining, by said one or more processors, a latent variable based at least on said first distribution and said second distribution;

estimating, by said one or more processors, one or more parameters of at least one bivariate distribution based on said latent variable, wherein said at least one bivariate distribution corresponds to a D-vine copula, wherein said D-vine copula is deterministic of one or more health conditions associated with each of said one or more second human subjects in said historical data, each health condition corresponding to a health condition category and to at least one of a disease risk, a disease symptom, an onset of a disease, a recovery from a disease, or an effect of medications for a disease, and said historical data corresponds to a multivariate dataset from which said one or more health conditions are identifiable based on said bivariate distribution;

training, by said one or more processors, a classifier based on said D-vine copula;

sorting, by said one or more processors, said received measure of said one or more physiological parameters associated with said first human subject into one or more of the health condition categories using the trained classifier;

assigning, by said one or more processors, a health condition profile to the first human subject, the profile comprising the one or more health conditions corresponding to the one or more categories into which the measure is sorted; and displaying the health condition profile on a display device.

2. The method of claim 1 further comprising determining, by said one or more processors, a third distribution associated with a third physiological parameter, from said one or more physiological parameters, based on said second distribution and a second conditional cumulative distribution of said transformed historical data, wherein said second conditional cumulative distribution is deterministic of at least an association between said third physiological parameter and one or more of said first physiological parameter or said second physiological parameter.

3. The method of claim 2, wherein said determination of said latent variable is further based on said third distribution.

4. The method of claim 1, wherein said one or more parameters are estimated by utilizing one of a Gibbs sampling technique or an Expectation-Maximization (EM) technique.

5. The method of claim 1, wherein said estimation of said one or more parameters is further based on an inverse Wishart distribution, parameterized using said latent variable.

6. The method of claim 1, wherein each of said first distribution and said second distribution is truncated based on a respective lower bound and a respective upper bound of said latent variable for each of said first physiological parameter and said second physiological parameter.

7. The method of claim 1, wherein said D-vine copula models a dependency between each pair of physiological parameters from said one or more physiological parameters.

8. The method of claim 1, wherein said bivariate distribution corresponds to a bivariate copula distribution including one or more of a T-student copula distribution, a Clayton copula distribution, a Gumbel copula distribution, or a Gaussian copula distribution.

9. The method of claim 1, wherein said one or more parameters comprise at least a covariance matrix associated with said at least one bivariate distribution.

10. The method of claim 1, wherein said ranking of said historical data corresponds to an extended rank likelihood.

11. A health condition profiling system, the system comprising:
a transceiver configured to receive a measure of one or more physiological parameters associated with said first human subject, wherein said one or more physiological parameters comprise at least one of an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood haemoglobin level, and a blood platelet count;
a display device; and
one or more processors configured to:
extract a historical data comprising a measure of said one or more physiological parameters associated with each of one or more second human subjects, wherein the historical data is missing values, comprises categorical data, or both;
determine a first distribution associated with a first physiological parameter, from said one or more physiological parameters, based on a marginal cumulative distribution of a transformed historical data, wherein said transformed historical data is determined by ranking of said historical data, and does not include any missing values or categorical data;
determine a second distribution associated with a second physiological parameter, from said one or more physiological parameters, based on said first distribution and a first conditional cumulative distribution of said transformed historical data, wherein said first conditional cumulative distribution is deterministic of at least an association between said first physiological parameter and said second physiological parameter;
determine a latent variable based at least on said first distribution and said second distribution;
estimate one or more parameters of at least one bivariate distribution based on said latent variable, wherein said at least one bivariate distribution corresponds to a D-vine copula, wherein said D-vine copula is deterministic of one or more health conditions associated with each of said one or more second human subjects in said historical data, each health condition corresponding to a health condition category and to at least one of a disease risk, a disease symptom, an onset of a disease, a recovery from a disease, or an effect of medications for a disease, and said historical data corresponds to a multivariate dataset from which said one or more health conditions are identifiable based on said bivariate distribution;
train a classifier based on said D-vine copula;
sort said received measure of said one or more physiological parameters associated with said first human subject into one or more of the health condition categories using the trained classifier;
assign, by said one or more processors, a health condition profile to the first human subject, the profile comprising the one or more health conditions corresponding to the one or more categories into which the measure is sorted; and
display the health condition profile on the display device.

12. The system of claim 11, wherein said one or more processors are further configured to determine a third distribution associated with a third physiological parameter, from said one or more physiological parameters, based on said second distribution and a second conditional cumulative distribution of said transformed historical data, wherein said second conditional cumulative distribution is deterministic of at least an association between said third physiological parameter and one or more of said first physiological parameter or said second physiological parameter.

13. The system of claim 12, wherein said determination of said latent variable is further based on said third distribution.

14. The system of claim 11, wherein said D-vine copula models a dependency between each pair of physiological parameters from said one or more physiological parameters.

15. The system of claim 11, wherein said bivariate distribution corresponds to a bivariate copula distribution including one or more of a T-student copula distribution, a Clayton copula distribution, a Gumbel copula distribution, or a Gaussian copula distribution.

16. The system of claim 11, wherein the system further comprises one or more biosensors and a human subject-computing device, the human subject-computing device comprises said one or more processors, the transceiver, and the display device, and the measure of one or more physiological parameters associated with the first human subject is received from the one or more biosensors.

17. The system of claim 11, wherein the system further comprises a database server and an application server, the application server comprises said one or more processors and the transceiver, and the measure of one or more physiological parameters associated with the first human subject is received from the database server.

18. A computer program product for use with a health condition profiling system comprising one or more processors, a transceiver, and a display, the computer program product comprising a non-transitory computer readable medium, wherein the non-transitory computer readable medium stores a computer program code for assigning a health condition profile to a first human subject, wherein the computer program code is executable by the one or more processors to:
- extract a historical data comprising a measure of said one or more physiological parameters associated with each of one or more second human subjects, wherein the historical data is missing values, comprises categorical data, or both;
- determine a first distribution associated with a first physiological parameter, from said one or more physiological parameters, based on a marginal cumulative distribution of a transformed historical data, wherein said transformed historical data is determined by ranking of said historical data, and does not include any missing values or categorical data;
- determine a second distribution associated with a second physiological parameter, from said one or more physiological parameters, based on said first distribution and a first conditional cumulative distribution of said transformed historical data, wherein said first conditional cumulative distribution is deterministic of at least an association between said first physiological parameter and said second physiological parameter;
- determine a latent variable based at least on said first distribution and said second distribution;
- estimate one or more parameters of at least one bivariate distribution based on said latent variable, wherein said at least one bivariate distribution corresponds to a D-vine copula, wherein said D-vine copula is deterministic of one or more health conditions associated with each of said one or more second human subjects in said historical data, each health condition corresponding to a health condition category and to at least one of a disease risk, a disease symptom, an onset of a disease, a recovery from a disease, or an effect of medications for a disease, and said historical data corresponds to a multivariate dataset from which said one or more health conditions are identifiable based on said bivariate distribution;
- train a classifier based on said D-vine copula;
- sort said received measure of said one or more physiological parameters associated with said first human subject into one or more of the health condition categories using the trained classifier;
- assign, by said one or more processors, a health condition profile to the first human subject, the profile comprising the one or more health conditions corresponding to the one or more categories into which the measure is sorted; and
- display the health condition profile on the display device,
- wherein the measure of one or more physiological parameters associated with said first human subject is received by the transceiver, and said one or more physiological parameters comprise at least one of an age, a cholesterol level, a heart rate, a blood pressure, a breath carbon-dioxide concentration, a breath oxygen concentration, a stroke score, a blood creatinine level, a blood albumin level, a blood sodium level, a total blood count, a blood glucose/sugar level, a blood haemoglobin level, and a blood platelet count.

* * * * *